United States Patent [19]

Cleland et al.

[11] Patent Number: 5,643,605
[45] Date of Patent: Jul. 1, 1997

[54] METHODS AND COMPOSITIONS FOR MICROENCAPSULATION OF ADJUVANTS

[75] Inventors: Jeffrey L. Cleland, San Carlos; Amy Lim, San Bruno; Michael Frank Powell, San Francisco, all of Calif.

[73] Assignee: Genentech, Inc., South San Francisco, Calif.

[21] Appl. No.: 460,363

[22] Filed: Jun. 2, 1995

Related U.S. Application Data

[63] Continuation of Ser. No. 143,332, Oct. 25, 1993, abandoned.
[51] Int. Cl.$^6$ ..................................................... A61K 9/50
[52] U.S. Cl. ........................ 424/489; 424/493; 424/499; 424/279.1
[58] Field of Search ................................. 424/489, 493, 424/499, 279.1

[56] References Cited

U.S. PATENT DOCUMENTS

| | | | |
|---|---|---|---|
| 4,293,539 | 10/1981 | Ludwig et al. | 424/19 |
| 4,524,067 | 6/1985 | Arichi et al. | 513/33 |
| 4,652,441 | 3/1987 | Okada et al. | 424/19 |
| 4,719,246 | 1/1988 | Murdoch et al. | 521/134 |
| 4,728,721 | 3/1988 | Yamamoto et al. | 528/361 |
| 4,767,628 | 8/1988 | Hutchinson et al. | 424/426 |
| 4,849,228 | 7/1989 | Yamamoto et al. | 424/422 |
| 4,897,268 | 1/1990 | Tice et al. | 424/486 |
| 4,902,515 | 2/1990 | Loomis et al. | 424/486 |
| 4,917,893 | 4/1990 | Okada et al. | 424/423 |
| 4,919,929 | 4/1990 | Beck et al. | 424/88 |
| 4,954,298 | 9/1990 | Yamamoto et al. | 264/4.6 |
| 4,962,091 | 10/1990 | Eppstein et al. | 514/2 |
| 4,990,336 | 2/1991 | Silvestri et al. | 424/426 |
| 5,008,116 | 4/1991 | Cahn | 424/491 |
| 5,015,476 | 5/1991 | Cochrum et al. | 424/423 |
| 5,057,540 | 10/1991 | Kensil et al. | 514/25 |
| 5,075,109 | 12/1991 | Tice et al. | 424/88 |
| 5,126,147 | 6/1992 | Silvestri et al. | 424/497 |
| 5,198,533 | 3/1993 | Schally et al. | 530/313 |
| 5,242,686 | 9/1993 | Chu et al. | 424/92 |

FOREIGN PATENT DOCUMENTS

| | | |
|---|---|---|
| 279688A2 | 8/1988 | European Pat. Off. . |
| 333523A2 | 9/1989 | European Pat. Off. . |
| 399843A2 | 11/1990 | European Pat. Off. . |
| 442671A2 | 8/1991 | European Pat. Off. . |
| 8803621 | 4/1990 | Sweden . |
| WO90/03984 | 4/1990 | WIPO . |
| WO91/15238 | 10/1991 | WIPO . |

OTHER PUBLICATIONS

O'Hagan et al. Biodegradable Microparticles—Immunology 73(2):239–242 (1991).
Tabata et al Activation of Macrophage—J. of Controlled Release 6: 189–204 (1987).
Alonso et al Determinants of Release—Pharm. Res. 10(7), 1993 pp. 945–953.
Jeffory et al., "The Preparation and Characterization of Poly(lactide–co–glycolide) Microparticles. II." Pharm. Res. 1:362–368 (1993).
Alonso et al., "Determinants of Release Rate of Tetanus Vaccine from Polyester Microspheres" Pharm. Res. 10 (7):945–953 (1993).
Arthur et al., "Challenge of chimpanzees (Pan troglodytes) immunized with human immunodeficiency virus envelope glycoprotein gp120" Journal of Virology 63(12):5046–5053 (1989).
Berman et al., "Human immunodeficiency virus type 1 challenge of chimpanzees immunized with recombinant envelope glycoprotein gp120" Proc. Natl. Acad. Sci. USA 85(14):5200–5204 (Jul. 1988).
Chang et al., "Biodegradable Semipermeable Microcapsules Containing Enzymes, Hormone, Vaccines, and Other Biologicals" J. Bioengineering 1:25–32 (1976).

(List continued on next page.)

Primary Examiner—Neil S. Levy
Attorney, Agent, or Firm—Jeffrey S. Kubinec

[57] ABSTRACT

Methods and compositions are provided for the encapsulation of adjuvants in PLGA microspheres for use as vaccines. Mixtures of microspheres are provided which release adjuvant at desired intervals to provide boosts with adjuvant.

9 Claims, 10 Drawing Sheets

OTHER PUBLICATIONS

Cohen, J., "Jitters Jeopardize AIDS Vaccine Trials" *Science* 262:980–981 (1993).

Cowsar et al., "Poly(lactide-co-glycolide) Microcapsules for Controlled Release of Steroids" *Methods in Enzymology* 112 (Drug and Enzyme Targ):101–116 (1985).

Eldridge et al., "Biodegradable and Biocompatible Poly-(DL-Lactide-Co-Glycolide) Micropheres as an Adjuvant for Staphylococcal Enterotoxin B Toxoid Which Enhances the Level of Toxin–Neutralizing Antibodies" *Infection and Immunity* 59(9):2978–2986 (1991).

Eldridge et al., "Biodegradable Micropheres As a Vaccine Delivery System" *Molecular Immuno.* 28(3):287–294 (1991).

Eldridge et al., "Biodegradable Poly(DL-lactide-coglycolide) Microshperes" *Res. Immunol.* 143(5):557–563 (1992).

Esparza et al., "Parameters Affecting the Immunogenicity of Microencapsulated Tetanus Toxoid" *Vaccine* 10(10):714–720 (1992).

Glaser, V., "Solving the HIV Vaccine Puzzle: Questions Still Outnumber the Answers" *Genetic Engineering News* pp. 15–30 (Nov. 1, 1993).

Hu et al., "Effect of immunization with a vaccinia–HIV env recombinant on HIV infection of chimpanzees" *Nature* 328(6132):721–723 (Aug. 1987).

Kensil et al., "Development of a genetically engineered vaccine agaisnts feline leukemia virus infection" *J. Amer. Veterinary Med. Assoc.* 199(10):1423–1427 (1991).

Kohn et al., "Single–step Immunization Using a Controlled Release, Biodegradable Polymer with Sustained Adjuvant Activity" *J. Immun. Methods* 95:31–38 (1986).

Newman et al., "Immunogenicity and Toxicity Testing of an Experimental HIV-1 Vaccine in Nonhuman Primates" *Aids Res. and Human. Retroviruses* 8(8):1413–1418 (1992).

Nunberg et al., "Adjuvant Formulations to Increase the Virus–neutralizing Antibody Response to HIV-1 rgp120 Subunit Vaccine" *Vaccines* (Annu. Meet.), Norrby et al., 11th edition, N.Y.:Cold Spring Harbor Lab vol. 94:23–27 (Mod. Approaches New 1994).

O'Hagan et al., "Biodegradable Microparticles as Controlled Release Antigen Delivery System" *Immunology* 73(2):239–242 (1991).

Payne et al., "Water–Soluble Phosphazene Polymers for Parenteral and Mucosal Vaccine Delivery" *Vaccine Design; The Subunit and Adjuvant Approach,* Powell et al., New York, NY:Plenum Press vol. 6:473–493 (1995).

Putney, S., "How Antibodies Block HIV Infection: Paths to and AIDS Vaccine" *TIBS* 17:191–196 (1992).

Sanders et al., "Controlled Release of a Luteinizing Hormone–Releasing Hormone Analogue from Poly (d,1–lactide–co–glycolide) Microspheres" *J. of Pharmaceutical Sciences* 73(9):1294–1297 (1984).

Singh et al., "Controlled Delivery of Diphtheria Toxoid Using Biodegradable Poly(D,L–Lactide) Microcapsules" *Pharmaceutical Research* 8(7):958–961 (1991).

Tabata et al., "Activation of Macrophage In Vitro to Acquire Antitumor Activity by a Muramyl Dipeptide Derivative Encapsulated in Microspheres Composed of Lactide Copolymer" *Journal of Controlled Release* 6:189–204 (1987).

Van Preis, "A Single–step Immunization by Sustained Antigen Release" *J. Immun. Methods* 28:193–197 (1979).

Wang et al., "Influence of formulation methods on the in vitro controlled release of protein from poly(ester) micropheres" *J. of Controlled Release* 17:23–32 (1991).

White et al., "A purified Saponin Acts as an Adjuvant for a T–independent Antigen" *Immunobiology of Proteins and Peptides VI,* M.Z. Atassi, New York:Plenum Press pp. 207–210 (1991).

Wu et al., "Saponin Adjuvant Enhancement of Antigen-Specific Immune Responses To An Experimental HIV-1 Vaccine" *J. of Immuno.* 148(5):1519–1525 (1992).

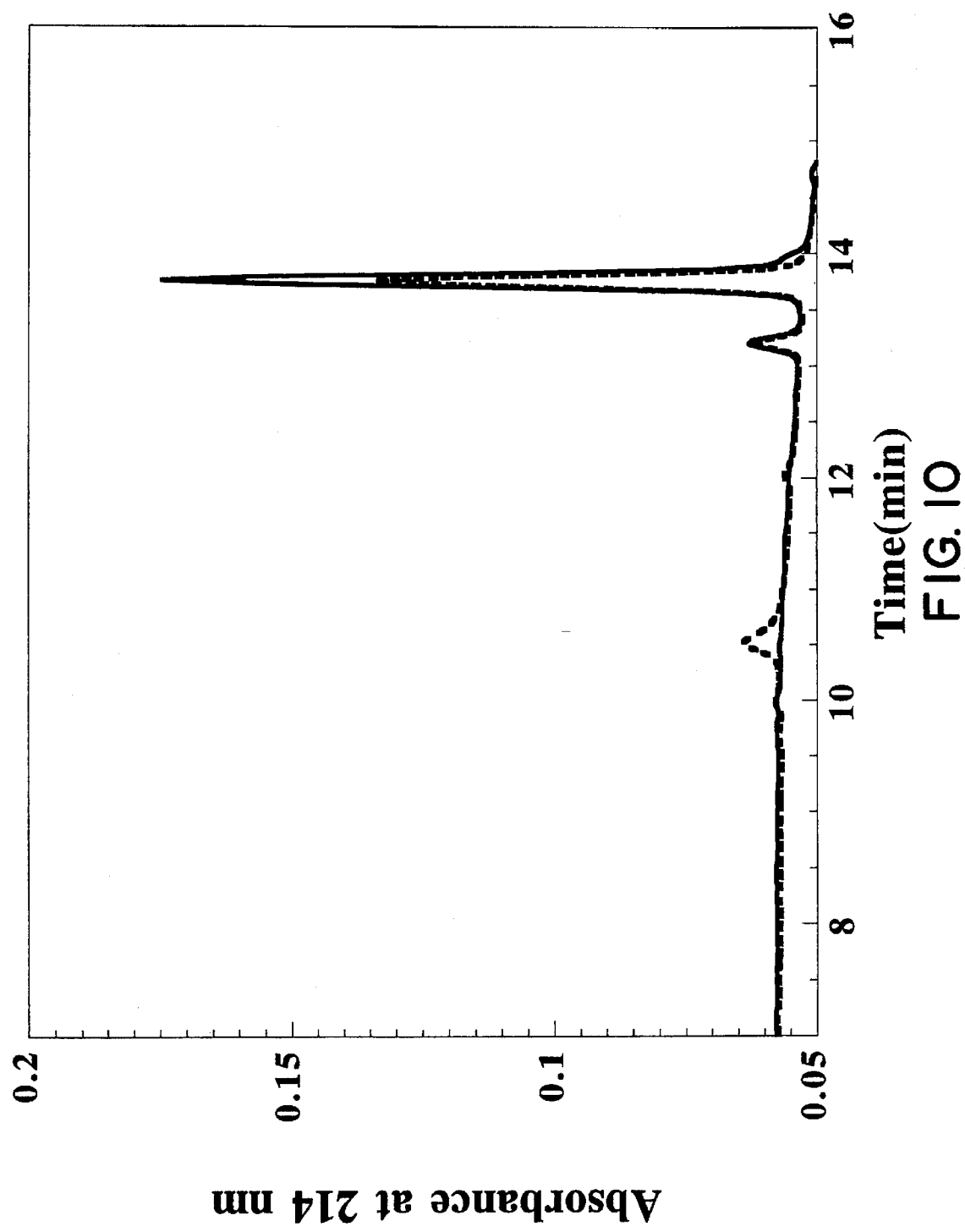

METHODS AND COMPOSITIONS FOR MICROENCAPSULATION OF ADJUVANTS

This application is a continuation of application Ser. No. 08/143,332, filed Oct. 25, 1993 now abandoned.

BACKGROUND OF THE INVENTION

1. Field of the Invention

This invention relates to the microencapsulation of adjuvants for use in therapeutic or prophylactic vaccine formulations.

2. Description of the Background and Related Art

The instant invention provides for the delivery of an adjuvant or adjuvants to a host in a microsphere format. The adjuvant or adjuvants can be delivered concomitantly with an antigen packaged within the same microsphere or in some other delivery format; alternatively, an antigen can be provided before or after the adjuvant-containing microspheres, or be packaged independently in microspheres.

The encapsulated adjuvant of the invention may be used in traditional immunization protocols typically requiring multiple exposures of the patient to an antigen, usually by injections of a vaccine formulation at intervals of weeks or months. In addition, the encapsulated adjuvant of the invention may be delivered to the patient in a formulation which releases the antigen and/or adjuvant in bursts spaced days to months apart, thereby reducing the need for multiple injections. The initial burst of antigen and/or adjuvant can be augmented by the addition of soluble antigen and/or adjuvant to the vaccine formulation. Mixtures of microspheres which release the antigen and/or adjuvant in a pulsatile manner with microspheres which release the antigen and/or adjuvant continuously can also be used.

Different antigens can be combined in the formulation, either within the same microspheres or as a mixture of microspheres, to provide a multivalent or multitarget vaccine. Adjuvants may also be combined, either within the same microspheres or as a mixture of microspheres, to provide an additive or synergistic effect. Furthermore, as microspheres can be designed to release a second burst of antigen and/or adjuvant ("autoboost") when desired, a single vaccine preparation can be designed so as to mix populations of microspheres which release their bursts of antigens and/or adjuvants at multiple prescribed intervals when such multiple challenges with antigen and/or adjuvant are desired.

Preferred adjuvants for use in the compositions and methods of the instant invention include saponins and their derivatives. For example, U.S. Pat. No. 5,057,540 discloses the uses of Quillaja saponins, a mixture of triterpene glycosides extracted from the bark of the tree *Quillaja saponaria*, as immune adjuvants. Saponins can be isolated from other plants, such as soybeans (U.S. Pat. No. 4,524,067). White et al. (*Immunology of Proteins and Peptides* VI, ed. M. Z. Atassi, Plenum Press, N.Y., 1991) disclose the use of QS21 as an adjuvant for a T-independent antigen. Wu et al. (*J. Immunol.* 148:1519–1525, 1992) disclose the use of QS21 as an adjuvant for the HIV-1 envelop protein gp160 in mice. Newman et al. (*AIDS Research and Human Retroviruses* 8:1413–1418, 1992) disclose the use of QS21 as an adjuvant for the HIV-1 envelop protein Gp160 in rhesus macaques. Kensil et al. (*J. Am. Vet. Med. Assoc.* 199:1423–1427, 1991) disclose the use of QS21 as an adjuvant for the feline leukemia virus subgroup A gp70 protein.

Polymer matrices for forming microspheres are also described in the literature. For example, Chang et al. (*Bioengineering* 1:25–32, 1976) disclose semipermeable microspheres containing enzymes, hormones, vaccines, and other biologicals. U.S. Pat. No. 5,075,109 discloses a method of potentiating an immune response by administering a mixture of at least two populations of microspheres containing bioactive agents such that one of the microsphere populations is sized between about 1 to 10 μm. U.S. Pat. No. 4,293,539 discloses a controlled release formulation of an active ingredient in a copolymer derived from about 60 to 95 weight percent lactic acid and about 40 to about 4 weight percent glycolic acid. U.S. Pat. No. 4,919,929 discloses the administration of an antigenic substance in a shaped structure of a biocompatible matrix material. U.S. Pat. No. 4,767,628 discloses composition comprising an active, acid stable polypeptide and a polylactide, which when placed in an aqueous physiological environment release the polypeptide at an approximately constant rate in an essentially monophasic manner. U.S. Pat. No. 4,962,091 discloses a microsuspension of water soluble macromolecular polypeptides in a polylactide matrix. U.S. Pat. Nos. 4,849,228 and 4,728,721 disclose a biodegradable, high molecular weight polymer characterized in that the content of water-soluble low molecular weight compounds, as calculated on the assumption that such compounds are monobasic acids, is less than 0.01 mole per 100 grams of high molecular weight polymer. U.S. Pat. Nos. 4,902,515 and 4,719,246 disclose polylactide compositions containing segments of poly(R-lactide) interlocked with segments of poly(S-lactide). U.S. Pat. No. 4,990,336 discloses a multiphasic sustained release system comprising allergen extract encapsulated in microspheres of bioerodible encapsulating polymer which permits a sustained, multiphasic release of the allergen. This system includes a first portion of allergen extract that upon injection is capable of being released in a manner whereby initial allergenicity is minimized to producing a mild local reaction similar to that normally observed with low doses of conventional allergen administration, and secondary portions of allergen extract that provide a substantially higher level of allergen extract in doses that could provide a serious reaction in the patient, but for the release of the first portion of allergen extract. U.S. Pat. No. 4,897,268 discloses a microcapsule delivery system wherein the ingredients are encapsulated in biodegradable copolymer excipients of varying mole ratios, such that delivery of the ingredients occurs at a constant rate over a prolonged period of time.

Various water-in-oil emulsions are described in the literature. Thus, for example, U.S. Pat. Nos. 4,917,893 and 4,652,441 disclose a microcapsule produced by preparing a water-in-oil emulsion comprising an inner aqueous layer containing a water-soluble drug, a drug-retaining substance, and an oil layer containing a polymer substance; the inner or aqueous layer is thickened or solidified to a viscosity of not lower than about 5000 centipoises. The resulting emulsion is subjected to in-water drying. U.S. Pat. No. 4,954,298 discloses the production of microcapsules by preparing a water-in-oil emulsion composed of a water-soluble drug-containing solution as the inner aqueous phase and a polymer-containing solution as the oil phase, dispersing the emulsion in an aqueous phase and subjected the resulting water-in-oil-in-water emulsion to an in-water drying, wherein the viscosity of the water-in-oil emulsion used in preparing the water-in-oil-in-water emulsion is adjusted to about 150 to about 10,000 centipoises.

Accordingly, it is an object of the invention to provide a microencapsulated adjuvant formulation for use in immunization of a patient against an antigen of interest.

This object and other objects will become apparent to those of ordinary skill in the art.

SUMMARY OF THE INVENTION

Accordingly, the instant invention provides for the delivery of an adjuvant or adjuvants to a host in a microsphere format. The adjuvant or adjuvants can be delivered concomitantly with an antigen packaged within the same microsphere or in some other delivery format; alternatively, an antigen can be provided before or after the adjuvant-containing microspheres, or be packaged independently in microspheres. In one embodiment of the invention, the microspheres of the instant invention release the adjuvant in a pulsatile manner. For example, the microspheres may release the adjuvant in three phases: an initial burst, a slow release, and a second burst. In a further embodiment of the invention, the adjuvant is continuously released from the microspheres. Preferred adjuvants for use in the compositions and methods of instant invention include saponins and their derivatives.

One aspect of the invention is a composition comprising poly(D-L-lactide-co-glycolide) (PLGA) microspheres encapsulating an adjuvant, wherein the ratio of lactide to glycolide is from about 100:0 to 0:100 weight percent;

the inherent viscosity of PLGA polymers used in the microspheres is about 0.1 to 1.2 dL/g;

the median diameter of the microspheres is from about 20 to 100 μm; and the adjuvant is released from the microspheres in a triphasic pattern, wherein about 0.5 to 95% of the adjuvant is released in an initial burst, about 0 to 50% is released over a period of about 1 to 200 days, and the remaining adjuvant is released in a second burst after about 1 to 200 days.

Another aspect of the invention is a composition comprising about one to 100 adjuvants encapsulated in a mixture of about two to 50 PLGA microsphere populations, wherein the ratio of lactide to glycolide is from about 100:0 to 0:100 weight percent;

the inherent viscosity of PLGA polymers used in the microspheres is about 0.1 to 1.2 dL/g;

the median diameter of the microspheres is from about 20 to 100 μm; and the adjuvant is released from the microspheres in a triphasic pattern, wherein about 0.5 to 95% of the adjuvant is released in an initial burst, about 0 to 50% is released over a period of about 1 to 200 days, and the remaining adjuvant is released in a second burst in one microsphere population after about 1 to 30 days, in a second microsphere population after about 30 to 90 days, and in additional microsphere populations after about 90 to 180 days.

Another aspect of the invention is a composition comprising poly(D-L-lactide-co-glycolide) (PLGA) microspheres encapsulating an adjuvant, wherein the ratio of lactide to glycolide is from about 100:0 to 0:100 weight percent;

the inherent viscosity of PLGA polymers used in the microspheres is about 0.1 to 1.2 dL/g;

the median diameter of the microspheres is from about 20 to 100 μm; and the adjuvant is continuously released from the microspheres over a period of about 1 to 200 days.

Another aspect of the invention is a method for encapsulating adjuvant in microspheres, comprising (a) dissolving PLGA polymer in an organic solvent to produce a solution;

(b) adding adjuvant to the solution of (a) to produce a PLGA-adjuvant mixture comprising a first emulsion;

(c) adding the mixture of step (b) to an emulsification bath to produce a microspheres comprising a second emulsion;

(d) hardening the microspheres of step (b) to produce hardened microspheres comprising encapsulated adjuvant.

BRIEF DESCRIPTION OF THE DRAWINGS

FIG. 10 is a reverse phase HPLC chromatogram comparing QS21 released from PLGA microspheres made with ethyl acetate and a static mixer to controls. The species which eluted at 13.4 and 13.9 minutes are isomers of the intact QS21. The earlier eluting peak (10.7 minutes) is derived from the hydrolysis of QS21. The solid line represents the control sample consisting of QS21 incubated at 37° C. in release media with placebo microspheres. The dashed line represents the chromatogram for the QS21 released initially from the PLGA microspheres.

DETAILED DESCRIPTION OF THE PREFERRED EMBODIMENTS

A. Definitions

Figure 1:
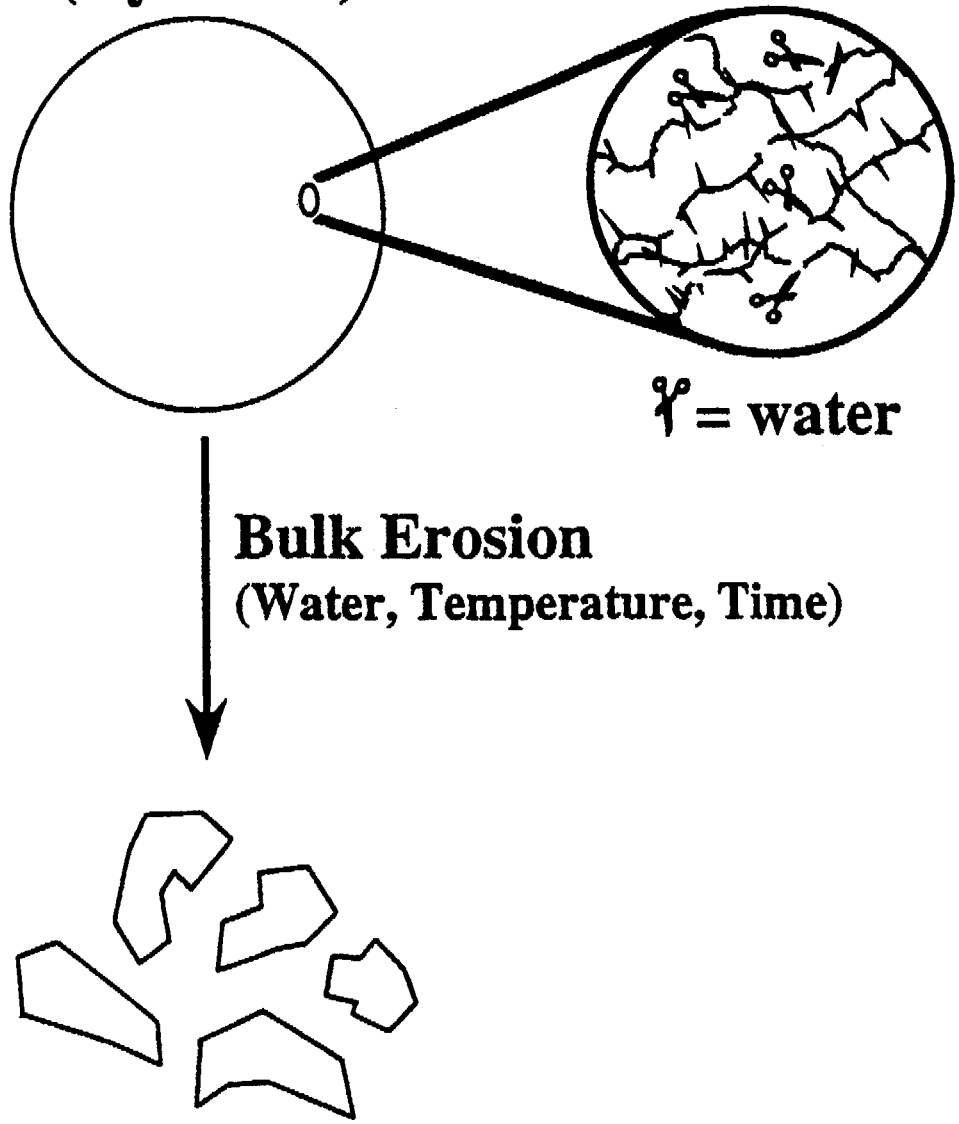
FIG. 1 is a diagram depicting the bulk erosion process for PLGA microspheres. PLGA microspheres are typically hydrated prior to administration. Water hydrolyzes the ester linkages in the PLGA backbone as shown in the inset diagram resulting in a bulk erosion of the polymer over time. The rate of hydrolysis depends upon the water content of the microspheres, the solvent environment (e.g., pH), and the temperature. The number of scissions in the polymer backbone required to cause fragmentation of the microspheres is dependent on the polymer molecular weight.

The terms "polylactide" and "PLGA" as used herein are used interchangeably and are intended to refer to a polymer of lactic acid alone, a polymer of glycolic acid alone, a mixture of such polymers, a copolymer of glycolic acid and lactic acid, a mixture of such copolymers, or a mixture of such polymers and copolymers. A preferred polymer matrix for formation of the microspheres of the instant invention is poly(D-L-lactide-co-glycolide).

The term "adjuvant" as used herein denotes a substance that in itself shares no immune epitopes with an antigen of interest, but which stimulates the immune response to the antigen of interest.

The term "antigen" as used herein denotes a compound containing one or more epitopes against which an immune response is desired. Typical antigens will include nucleic acids, proteins, polypeptides, peptides, polysaccharides, and hapten conjugates. Complex mixtures of antigens are also included in this definition, such as whole killed cells, bacteria, or viruses, or fractions thereof.

The term "therapeutic amount" as used herein denotes an amount that prevents or ameliorates symptoms of a disorder or responsive pathologic physiological condition. In certain embodiments of the present invention, the amount administered is sufficient to raise an immune response which substantially prevents infection or the spread of the infectious agent within the recipient.

The term "polyol" as used herein denotes a hydrocarbon including at least two hydroxyls bonded to carbon atoms. Polyols can include other functional groups. Examples of polyols useful for practicing the instant invention include sugar alcohols such as mannitol and trehalose, and polyethers.

The term "polyether" as used herein denotes a hydrocarbon containing at least three ether bonds. Polyethers can include other functional groups. Polyethers useful for practicing the invention include polyethylene glycol (PEG).

The term "dry antigen" or "dry adjuvant" as used herein denotes an antigen or adjuvant which has been subjected to a drying procedure such as lyophilization such that at least about 50% of its moisture has been removed.

The term "encapsulation" as used herein denotes a method for formulating an active agent such as an adjuvant or antigen into a composition useful for controlled release of the active agent. Examples of encapsulating materials useful in the instant invention include polymers or copolymers of lactic and glycolic acids, or mixtures of such polymers and/or copolymers, commonly referred to as "polylactides" or "PLGA", although any polyester or other encapsulating material may be used. The term "coencapsulation" as used herein refers to the incorporation of two or more active agents, such as adjuvant and antigen, more than one antigen, more than one adjuvant, etc., into the same microsphere.

The term "admixing" as used herein denotes the addition of an excipient to an antigen or adjuvant of interest, such as by mixing of dry reagents or mixing of a dry reagent with a reagent in solution or suspension, or mixing of aqueous formulations of reagents.

The term "excipient" as used herein denotes a non-therapeutic carrier added to a pharmaceutical composition that is pharmaceutically acceptable, i.e., non-toxic to recipients at the dosages and concentrations employed. Suitable excipients and their formulation are described in *Remington's Pharmaceutical Sciences*, 16th ed., 1980, Mack Publishing Co., Oslo, et al., ed.

The term "organic solvent" as used herein is intended to mean any solvent containing carbon compounds. Exemplary organic solvents include halogenated hydrocarbons, ethers, esters, alcohols and ketones, such as,for example, methylene chloride, ethyl acetate, a mixture of ethyl acetate and benzyl alcohol or acetone, dimethyl sulfoxide, tetrahydrofuran, dimethylformamide, and ethanol.

"Treating" an antigen or adjuvant with an organic solvent as used herein refers to mixing a dry antigen or adjuvant with an organic solvent, or making an emulsion of an antigen or adjuvant in an aqueous formulation with an organic solvent, creating an interface between an antigen or adjuvant in an aqueous formulation with an organic solvent, or extracting an antigen or adjuvant from an aqueous formulation with an organic solvent.

"Polypeptide" as used herein refers generally to peptides and proteins having at least about two amino acids.

"Vaccine" as used herein refers to a formulation of an antigen intended to provide a prophylactic or therapeutic response in a host when the host is challenged with the antigen. Exemplary vaccines include vaccines directed against such diseases as hepatitis, polio, herpes, foot and mouth disease, diphtheria, tetanus, pertussis, and malaria, and infection with such agents as cytomegalovirus, HIV, and Haemophilus sp. Preferred vaccines herein include gp120, vaccinia virus-HIV env recombinant vaccine, and gp160.

"Fluidized bed" as used herein refers generally to a bed of granular particles through which a stream of gas is slowly flowing upward, suck that with further increase in gas velocity, the pores and channels enlarge and the particles become more widely separated. Included in this definition are fluidized- or fixed-bed configurations, including but not limited to slurry and trickle-bed reactor systems. Gases used in the fluidized bed are preferably nitrogen, oxygen, and carbon dioxide, although any dry gas which facilitates removal of water and/or other solvents may be used. The methodology for designing a fluidized- or fixed-bed system is widely known in the art, as are examples of fluidized-bed systems useful in practicing the instant invention (see, for example, Perry & Chilton (Chemical Engineers' Handbook, R. H. Perry & C. H. Chilton, Eds., Fifth Edition, pp. 4-20–4-40, 5-52–5-55, 1973).

The term "harden" as used herein in reference to microspheres refers to the extraction of excess organic solvent from the polymer phase.

B. General Methods

Figure 3:
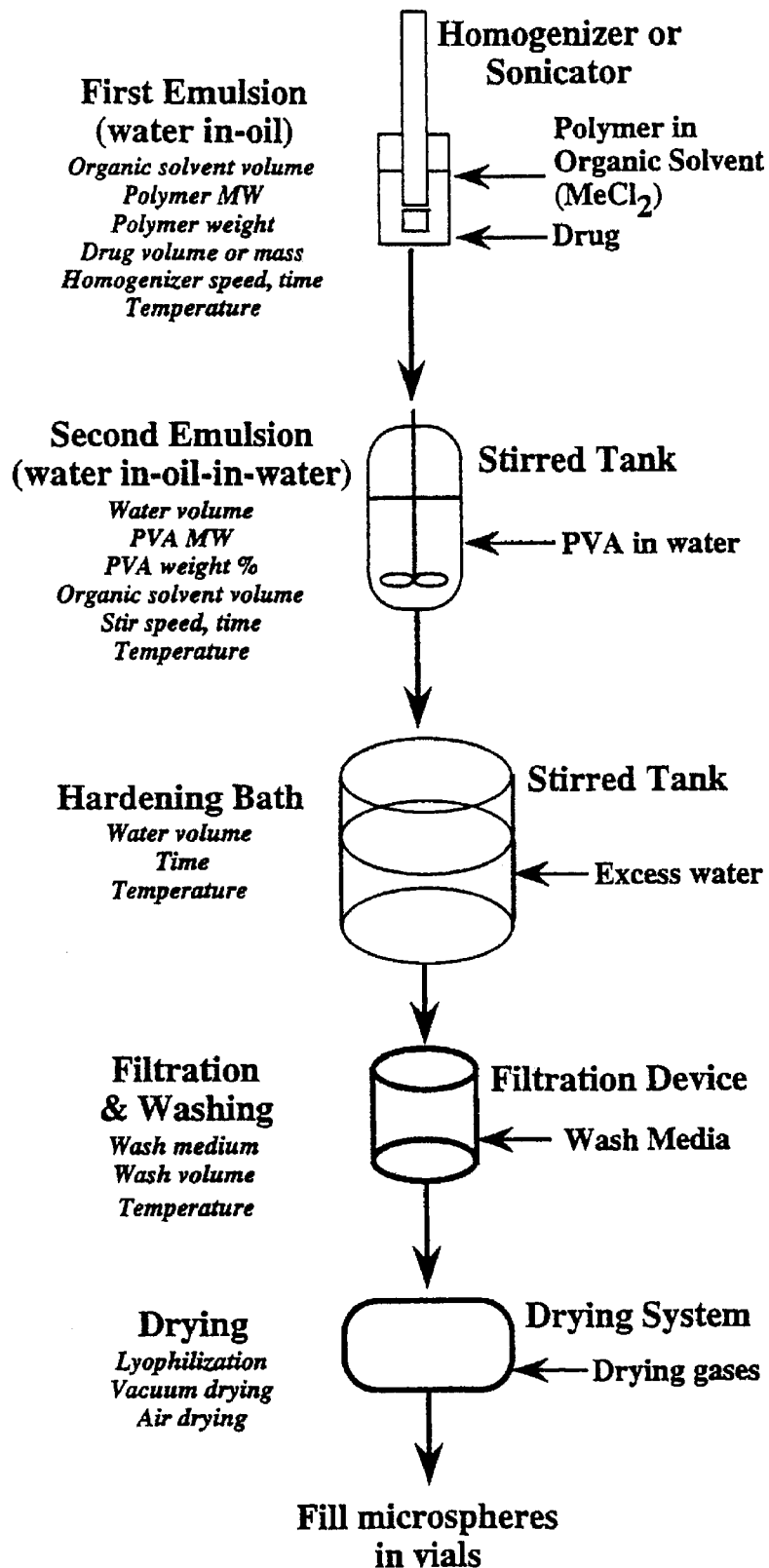
FIG. 3 is a diagram depicting the microsphere production process using a double emulsion method. PLGA polymers at different molecular weights were added to methylene chloride and allowed to dissolve. A solution of adjuvant was then injected into the methylene chloride while homogenizing. The homogenized solution was added to a polyvinyl alcohol (PVA) solution. The PVA solution was saturated with methylene chloride (1.5% v/v) for some experiments. The PVA and polymer solutions were mixed in a one liter fermenter to form the final water-in-oil-in-water emulsion. The resulting microspheres were then transferred to the hardening bath which contained an excess of water to extract the remaining methylene chloride. The hardened microspheres were then washed and dried by lyophilization or low temperature (5° C.) nitrogen (fluidized bed) or vacuum drying to produce the final microspheres for in vivo and in vitro analysis. The items listed in italics are the variables for each process step.

In general, microencapsulation of an antigen or adjuvant is performed according to the protocol briefly outlined in FIG. 3. In summary, PLGA of the desired ratio of lactide to glycolide (about 100:0 to 0:100 weight percent, more preferably, about 65:35 to 35:65, most preferably about 50:50) and inherent viscosity (generally about 0.1 to 1.2 dL/g, preferably about 0.2 to 0.8 dL/g) is first dissolved in an organic solvent such as methylene chloride, or ethyl acetate with or without benzyl alcohol or acetone to the desired concentration (generally about 0.05 to 1.0 g/mL, preferably about 0.3 to 0.6 g/mL). A concentrated antigen or adjuvant solution (for example, typically at least 0.1 mg/mL for polypeptides, preferably greater than about 100 mg/mL, depending, for example, on the type of polypeptide and the desired core loading) is then suitably injected (such as with a 25 gauge needle) into the polymer solution while homogenizing at about 15,000 to 25,000 rpm. Dry antigen or adjuvant can be used in place of aqueous antigen or adjuvant. After homogenization (generally about 0.5 to 5 minutes, more preferably for 1 minute), the emulsion is added to the reaction kettle (emulsification bath) or static mixer (not shown) to form a second emulsion. The emulsification bath is typically a polyvinyl alcohol solution, optionally including ethyl acetate. The reaction kettle is mixed at high speed (generally about 1700 to 2500 rpm) to generate small microspheres (about 20 to 100 µm median diameter). The second emulsion is transferred to a hardening bath after a sufficient period of time, generally about 0.5 to 10 minutes, preferably about 1 minute, and allowed to gently mix for a suitable time, generally about 1 to 24 hours, preferably about 1 hour. When hardening is complete, the microspheres are prefiltered (such as with a 150 µm mesh), concentrated and diafiltered. Diafiltering is suitably accomplished in an Amicon stirred cell (2500 mL), preferably with about a 16 or 20 µm filter. The microspheres are washed, typically with about 1 to 100 L, preferably about 15 L of prefiltered water and typically with about 1 to 100 L, more preferably 15 L of 0.1% Tween® 20. The final microspheres are removed from the filter and resuspended in water and filled in vials, preferably at about 500 µL/vial in 3 cc vials. The microspheres can then be dried. Drying includes such methods as lyophilzation, vacuum drying, and fluidized bed drying.

Three other exemplary methods can be employed to produce microspheres. The first method utilizes a solvent evaporation technique. A solid or liquid active agent is added to an organic solvent containing the polymer. The active agent is then emulsified in the organic solvent. This emulsion is then sprayed onto a surface to create microspheres and the residual organic solvent is removed under vacuum. The second method involves a phase-separation process, often referred to as coacervation. A first emulsion of aqueous or solid active agent dispersed in organic solvent containing the polymer is added to a solution of non-solvent, usually silicone oil. By employing solvents that do not dissolve the polymer (non-solvents) but extract the organic solvent used to dissolve the polymer (e.g. methylene chloride or ethyl acetate), the polymer then precipitates out of solution and will form microspheres if the process occurs while mixing. The third method utilizes a coating technique. A first emulsion comprising the active agent dispersed in a organic solvent with the polymer is processed through an air-suspension coater apparatus resulting in the final microspheres.

When antigen and adjuvant are to be administered from within the same microspheres, a solution containing both antigen and adjuvant or solutions containing antigen and adjuvant separately can be added to the polymer solution. Similarly, soluble antigen and dry adjuvant, dry antigen and soluble adjuvant, or dry antigen and dry adjuvant, can be used. The microspheres of the instant invention are preferably formed by a water-in-oil-in-water emulsion process.

In general, both aqueous formulations and dry polypeptide antigens or adjuvants can be admixed with an excipient to provide a stabilizing effect before treatment with an organic solvent such as methylene chloride. An aqueous formulation of a polypeptide can be a polypeptide in suspension or in solution. Typically an aqueous formulation of the excipient will be added to an aqueous formulation of the polypeptide, although a dry excipient can be added, and vice-versa. An aqueous formulation of a polypeptide and an excipient can be also dried by lyophilization or other means. Such dried formulations can be reconstituted into aqueous formulations before treatment with an organic solvent.

The excipient used to stabilize a polypeptide antigen of interest will typically be a polyol of a molecular weight less than about 70,000 kD. Examples of polyols that can be used include trehalose (copending U.S. Ser. No. 08/021,421 filed Feb. 23, 1993), mannitol, and polyethylene glycol (PEG). Typically, the mass ratio of trehalose to polypeptide will be about 1000:1 to 1:1000, preferably about 100:1 to 1:100, more preferably about 1:1 to 1:10, most preferably about 1:3 to 1:4. Typical mass ratios of mannitol to polypeptide will be about 100:1 to 1:100, preferably about 1:1 to 1:10, more preferably about 1:1 to 1:2. Typically, the mass ratio of PEG to polypeptide will be about 100:1 to 1:100, preferably about 1:1 to 1:10. Preferred ratios are chosen on the basis of an excipient concentration which allows maximum solubility of polypeptide with minimum denaturation of the polypeptide.

The formulations of the instant invention can contain a preservative, a buffer or buffers, multiple excipients, such as polyethylene glycol (PEG) in addition to trehalose or mannitol, or a nonionic surfactant such as Tween® surfactant. Non-ionic surfactants include polysorbates, such as polysorbate 20 or 80, and the poloxamers, such as poloxamer 184 or 188, Pluronic® polyols, and other ethylene oxide/propylene oxide block copolymers, etc. Amounts effective to provide a stable, aqueous formulation will be used, usually in the range of from about 0.1%(w/v) to about 30%(w/v).

The pH of the formulations of this invention is generally about 5 to 8, preferably about 6.5 to 7.5. Suitable buffers to achieve this pH include, for example, phosphate, Tris, citrate, succinate, acetate, or histidine buffers, depending on the pH desired. Preferably, the buffer is in the range of about 2 mM to about 100 mM.

Examples of suitable preservatives for the formulation include phenol, benzyl alcohol, meta-cresol, methyl paraben, propyl paraben, benzalconium chloride, and benzethonium chloride. Preferred preservatives include about 0.2 to 0.4%(w/v) phenol and about 0.7 to 1%(w/v) benzyl alcohol, although the type of preservative and the concentration range are not critical.

In general, the formulations of the subject invention can contain other components in amounts not detracting from the preparation of stable forms and in amounts suitable for effective, safe pharmaceutical administration. For example, other pharmaceutically acceptable excipients well known to those skilled in the art can form a part of the subject compositions. These include, for example, salts, various bulking agents, additional buffering agents, chelating agents, antioxidants, cosolvents and the like; specific examples of these include tris-(hydroxymethyl) aminomethane salts ("Tris buffer"), and disodium edetate.

Exemplary adjuvants of interest useful in the instant invention include saponins such as QS21, muramyl dipeptide, muramyl tripeptide, and compounds having a muramyl peptide core, mycobacterial extracts, aluminum hydroxide, proteins such as gamma interferon and tumor necrosis factor, phosphatidyl choline, squalene, Pluronic® polyols, and Freund's adjuvant (a mineral oil emulsion) (see the Background section of this application for references). Although antigen is desirably administered with an adjuvant, in situations where the initial inoculation is delivered with an adjuvant, boosts with antigen may not require adjuvant. PLGA or other polymers can also serve as adjuvants.

Antigens of interest useful herein include, for example, HIV antigens such as gp120, gp160, gag, pol, Nef, Tat, and Rev; malaria antigens such as CS proteins and sporozoite 2; hepatitis B antigens, including Pre-S1, Pre-S2, HBcAg, HBsAg, and HBeAg; influenza antigens such as HA, NP, and NA; hepatitis A surface antigens; Herpes virus antigens such as EBV gp340, EBV gp85, HSV gB, HSV gD, HSV gH, and HSV early protein product; cytomegalovirus antigens such as gB, gH, and IE protein gP72; respiratory syncytial virus antigens such as F protein, G protein, and N protein. Polypeptides or protein fragments defining immune epitopes, and amino acid variants of proteins, polypeptides, or peptides, can be used in place of full length proteins. Polypeptides and peptides can also be conjugated to haptens.

Typically, an antigen of interest will be formulated in PLGA microspheres to provide a desired period of time between the first and second bursts of antigen and to provide a desired amount of antigen in each burst. The amount of antigen in the initial burst can be augmented by soluble antigen in the formulation. Preferably, an adjuvant is microencapsulated, although soluble adjuvant can also be administered to the patient. Microspheres containing adjuvant can be formulated to release adjuvant in a pulsatile manner or to continuously release adjuvant and can be used alone or in any combination with soluble antigen, microspheres which continuously release antigen, or microspheres which release antigen in a pulsatile manner.

The microspheres, soluble antigen, and/or adjuvant are placed into pharmaceutically acceptable, sterile, isotonic formulations together with any required cofactors, and optionally are administered by standard means well known in the field. Microsphere formulations are typically stored as a dry powder.

The amount of adjuvant delivered to the patient to be used in therapy will be formulated and dosages established in a fashion consistent with good medical practice taking into account the disorder to be treated, the condition of the individual patient, the site of delivery, the method of administration and other factors known to practitioners. Generally, doses of from about 0.1 to 1000 µg per patient per administration are preferred. Different dosages can be utilized during a series of sequential inoculations; the practitioner can administer an initial inoculation and then boost with relatively smaller doses of adjuvant.

It is envisioned that injections (intramuscular or subcutaneous) will be the primary route for therapeutic administration of the encapsulated adjuvant of this invention, although intravenous delivery, or delivery through catheter or other surgical tubing is also used. Alternative routes include suspensions, tablets, capsules and the like for oral administration, commercially available nebulizers for liquid formulations, and inhalation of lyophilized or aerosolized microcapsules, and suppositories for rectal or vaginal administration. Liquid formulations can be utilized after reconstitution from powder formulations.

The adequacy of the vaccination parameters chosen, e.g. dose, schedule, adjuvant choice and the like, can be determined by taking aliquots of serum from the patient and assaying antibody titers during the course of the immunization program. Alternatively, the presence of T cells or other cells of the immune system can be monitored by conventional methods. In addition, the clinical condition of the patient can be monitored for the desired effect, e.g. antiinfective effect. If inadequate vaccination is achieved then the patient can be boosted with further vaccinations and the vaccination parameters can be modified in a fashion expected to potentiate the immune response, e.g. increase the amount of antigen and/or adjuvant, complex the antigen with a carrier or conjugate it to an immunogenic protein, or vary the route of administration.

The degradation rate for the microspheres of the invention is determined in part by the ratio of lactide to glycolide in the polymer and the molecular weight of the polymer. Polymers of different molecular weights (or inherent viscosities) can be mixed to yield a desired pulsatile degradation profile. Furthermore, populations of microspheres designed to have the second burst occur at different times can be mixed together to provide multiple challenges with the antigen and/or adjuvant at desired intervals. Similarly, mixtures of antigens and/or adjuvants can be provided either together in the same microspheres or as mixtures of microspheres to provide multivalent or combination vaccines. Thus, for example, rather than receive three immunizations with traditional DTP (diphtheria, tetanus, and pertussis) vaccine at 2, 4, and 6 months, a single microencapsulated vaccine can be provided with microspheres that provide second bursts at 2, 4, and 6 months. Microspheres can be formulated which provide adjuvant at similar pulsatile intervals, or for continuous release over a period of, for example, 1 to 200 days.

The microspheres of the instant invention can be prepared in any desired size, ranging from about 0.1 to upwards of about 100 μm in diameter, by varying process parameters such as stir speed, volume of solvent used in the second emulsion step, temperature, concentration of PLGA, and inherent viscosity of the PLGA polymers. The relationship of these parameters is discussed in detail below. The microspheres of the instant invention are of a median diameter of generally about 20 to 100 μm, preferably about 20 to 50 μm, more preferably 30 μm.

Further details of the invention can be found in the following examples, which further define the scope of the invention. All references cited herein are expressly incorporated by reference in their entirety.

EXAMPLES

I. Materials and Methods

A. PLGA

Poly(D-L-lactide-co-glycolide) (PLGA) was purchased from both Boehringer Ingelheim (BI) and Medisorb Technologies International L.P. (MTI). Various molecular weights and lactide to glycolide ratios of PLGA were used to assess the effect of these parameters on the microsphere properties (Table 1). PLGA at 12 kDa and 100 kDa were obtained from BI, and PLGA at 18 kDa and 100 kDa were obtained from MTI. The polymer compositions were either 50:50 or 75:25 lactide:glycolide. The 10% polyvinyl alcohol solution (PVA Airvol 205, Air Products) was prepared by dissolving solid PVA in warm water (about 80° C.). The final PVA solution was filtered with 0.22 μm Millipak filters from Millipore. Methylene chloride (technical grade) was purchased from Baxter S/P. Ethyl acetate was obtained as HPLC grade (Baxter B & J Brand). N-acetyl muramyl-L-alanyl-D-isoglutamine (MDP) was supplied by Sigma Chemical Co. (Lot# 90H02031).

TABLE 1

Polylactide-coglycolide (PLGA) Used for Microsphere Formulations

| Vendor | Inherent Viscosity[a] (dL/g) | Molecular Weight[b] (kDa) | Lactide:Glycolide[c] | Lot# |
|---|---|---|---|---|
| BI | 0.21 | 12 | 48:52 | 15068 |
|  | N.A. | 12 | 75:25* | 15056 |
|  | 0.76 | 100 | 48:52 | 05076 |
|  | N.A. | 100 | 75:25* | 15045 |
| MTI | 0.24 | 18 | 50:50* | 622-84 |
|  | 0.21 | 24 | 72:27 | 622-92A |
|  | 0.75 | 95 | 51:49 | S21268174 |
|  | 0.62 | 100* | 74:26 | S2101SE168 |

[a]Inherent viscosity of polymers dissolved in chloroform. N.A. denotes not available.
[b]Molecular weights were determined by using gel permeation chromatography with polystyrene standards. Polymers dissolved and analyzed in methylene chloride at room temperature. Molecular weight shown is a weight average value. Values for BI polymers are approximate since specifications were not included with the product*.
[c]Lactide:glycolide molar ratio in PLGA as measured by vendor is usually within 3% of specifications. Specifications are either 50:50 or 75:25 lactide:glycolide for these polymers.
*Estimated values based on specifications for polymer type. Actual values not available.

B. Preparation of RGP120

MN rgp120 (Lot#Y16531/G90557) was supplied in bulk at 2.3 mg/mL protein in 20 mM Tris, 0.120M NaCl, pH 7.4 from Genentech, Inc. It was concentrated with a Amicon stirred cell concentrator using a YM 30,000 MW cutoff membrane at 4° C. to a final concentration of 154 mg/mL and stored at 2° to 8° C.

C. Preparation of OS21

Lyophilized QS21 (about 80% pure, Lot# D1949) was supplied from Cambridge Biotech (Cambridge, Mass.). QS21 was prepared at 200 mg/mL by dissolving the lyophilized QS21 powder in 50% ethanol/water. QS21 was also dissolved in 50% ethanol with 20% Tween® 20 in an attempt to increase the encapsulation efficiency and release rate. The QS21 solutions were prepared and used on the same day as the encapsulation.

D. Microencapsulation of GP120

The production of rgp120 microspheres was performed by a double emulsion water-in-oil-in-water (WOW) as discussed above in general terms. More specifically, the PLGA concentrations in methylene chloride were 0.3 or 0.6 g/mL, and the first emulsion was homogenized at 15,000 rpm and 0° to 1° C. in a water bath. After 1 minute of homogenization, the first emulsion (10 mL) was added to 900 mL of 10% PVA solution containing 1.5% methylene chloride and emulsified at high speed (800 to 2500 rpm) for 1 minute in the reaction kettle (2° to 8° C.). To improve the encapsulation efficiency, the second emulsion was also performed with 10% PVA that did not contain methylene chloride and the temperature of the second emulsion was maintained at 0° to 3° C. To achieve the reduced temperature, the ethylene glycol in the cooling jacket of the reaction kettle was kept at −15° C. The second emulsion was then transferred to the hardening bath containing 12 liters of prefiltered water (MilliQ water system, Millipore Corp.) at 2° to 8° C. The microspheres were allowed to harden for 1 hour. The hardened microspheres were concentrated to about 1.5 L and diafiltered against 15 L of prefiltered water followed by 15 L of 0.1% Tween® 20The Amicon stirred cell (2.5 L) was operated with different filter systems depending upon the desired particle size. After washing, the microspheres were concentrated to dryness. The concentrated microspheres were removed from the filter by using a cell scraper and resuspended in prefiltered water to about 0.3 gm/mL.

Figure 4:
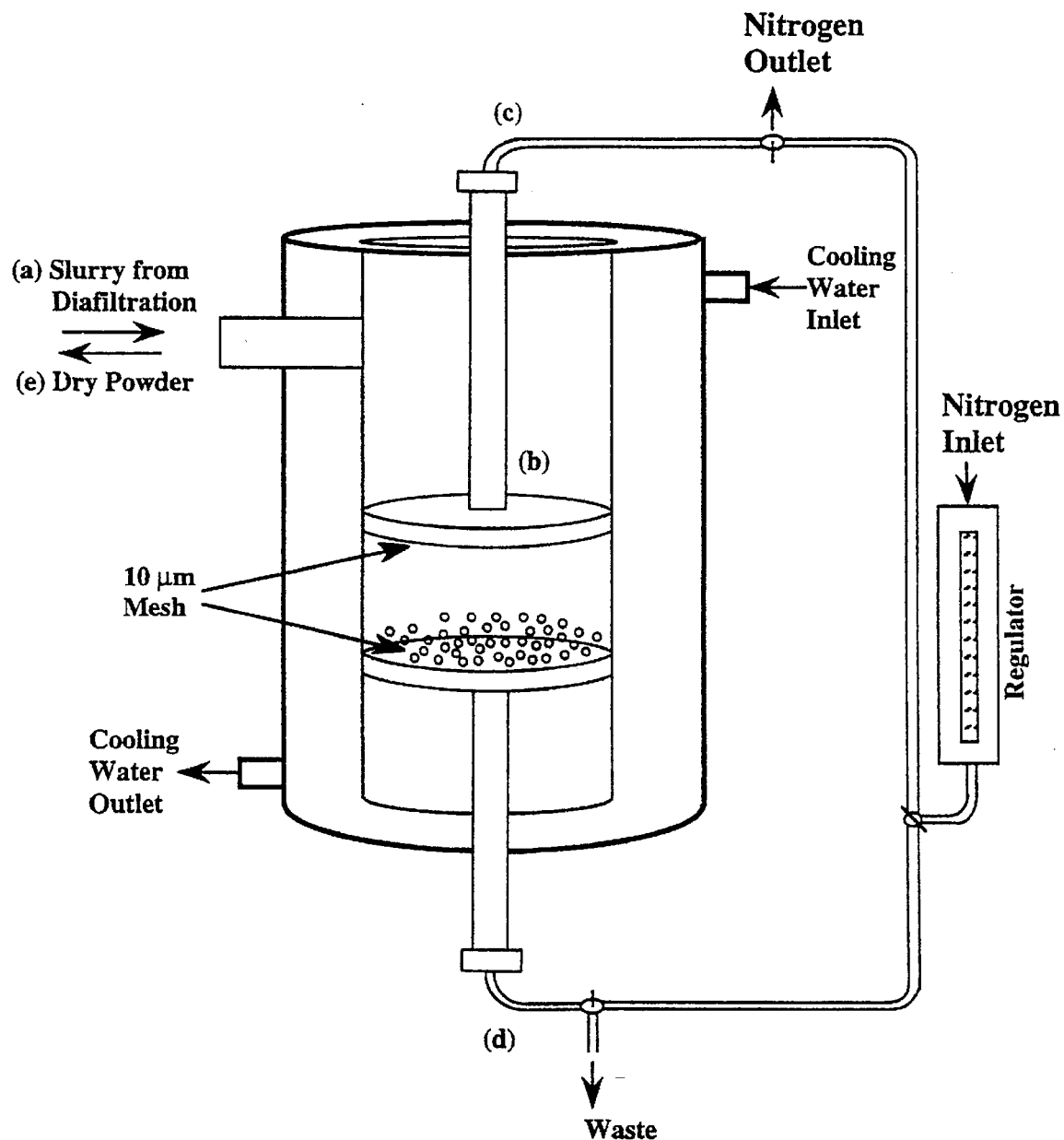
FIG. 4 is a diagram depicting an air lift (fluidized bed) drying system for nitrogen drying of PLGA microspheres. (a) Slurry from a diafiltration unit is pumped into the chamber with the upper piston (b) above the inlet. The upper piston is then moved down and the excess liquid is pressurized out by applying nitrogen through the upper inlet (c). The airflow is then redirected to suspend the microspheres by purging with nitrogen through the lower inlet (d) and releasing the nitrogen through the upper inlet (c). After complete drying (1 to 2 days), the dry powder is removed by placing a collection vessel (side arm flask, not shown) on the outlet, moving the upper piston (b) above the outlet, and applying nitrogen pressure at the lower inlet (d) while pulling a vacuum on the collection vessel. Alternatively, the drier can be designed with both pistons welded in place and the upper piston located above the inlet for the slurry. After pumping in the slurry, the slurry outlet side arm is then sealed by a valve during drying.

Three different drying methods were used to dry the microspheres: lyophilization, vacuum drying, and fluidized bed drying by using the system shown in FIG. 4 or a 5 mL Amicon stirred cell. A suspension of the final microspheres was added to the airlift drier (FIG. 4) or a stirred cell and the residual liquid was removed by applying a slight (about 2 psi) nitrogen pressure to the column (nitrogen flow downward). After the residual liquid was removed, the nitrogen flow was directed upward through the airlift drier or Amicon stirred cell to suspend the microspheres. The nitrogen line was connected to a prefilter (0.22 μm) for the stirred cell and a desiccating column with prefilters for the airlift drier. A water bath was connected to the jacket of the airlift drier to maintain the system at 5° C. The Amicon stirred cell drying was performed in a 2° to 8° C. cold room. A few batches were also vacuum dried at higher temperatures (10° C. or 15° C.) to speed up the drying process without increasing the initial burst.

E. Encapsulation of OS21

QS21 was dissolved in 50% ethanol with or without Tween® 20 as described above. As with the rgp120 solutions, the QS21 solution was injected into the polymer phase. For the microsphere preparations containing both rgp120 and QS21, the rgp120 solution was injected into the polymer phase after the QS21 solution to reduce the potential interaction between rgp120 and the ethanol in the QS21 solution.

The encapsulation of QS21 by itself was performed by two different water-in-oil-in-water methods. The first method was performed with methylene chloride and a stirred tank as the reaction kettle. A 50:50 mass ratio of 100 kDa PLGA (Lot# 15045; 75:25 lactide:glycolide) and 12 kDa PLGA (Lot# 15056; 75:25 lactide:glycolide) from BI was used for the encapsulation. A total PLGA mass of 3 g was dissolved in 5 mL of methylene chloride, after which 0.5 mL of QS21 solution (200 mg/mL QS21, 50% ethanol) was injected into the PLGA solution at 1° C. while homogenizing at 15,000 rpm. The mixture was homogenized for 1 minute and then transferred by injection into a 1-liter fermentor (LH Fermentation) containing 10% PVA. The fermentor was operated at 2500 rpm and 1° C. during and after addition of the QS21/PLGA solution. After mixing for 1 minute, the microspheres were transferred to 12 L of prefiltered distilled water (MilliQ water, Millipore Corp.) in a stirred tank at 2°–8° C. The microspheres were allowed to harden for 1 hour at 2°–8° C. After hardening, the microspheres were filtered with a 150- μm nylon mesh and then ultrafiltered in a 2.5-L Amicon stirred cell with a 0.22- μm filter. The microspheres were then diafiltered with 15 L of prefiltered distilled water (MilliQ water, Millipore Corp.) and 15 L of 0.1% Tween 20, and then were vacuum dried at 2°–8° C. for 7 days.

The second method for encapsulation of QS21 included the use of ethyl acetate instead of methylene chloride and a static mixer in place of a reaction kettle for formation of the final emulsion. A 50:50 mass ratio of 12 kDa (0.2 IV, 65:35 lactide:glycolide, Lot# MPE93-2) and 100 kDa (0.61 IV, 65:35 lactide:glycolide, Lot# S2073S1158) PLGA from MTI was used for the encapsulation. The total PLGA mass (3 g) was dissolved in 10 mL of ethyl acetate. The PLGA solution was cooled to 1° C. and 1.0 mL of the QS21 solution (200 mg/mL QS21, 60% ethanol) was then injected while homogenizing at 15,000 rpm. The PLGA solution was homogenized for an additional minute after the injection of QS21The homogenized QS21/PLGA solution was then emulsified with PVA in a static mixer to form the microspheres. This emulsification step was performed by pumping 9% PVA (10% ethyl acetate, 3° C.) at 1.5 L/minute into a static mixer (Koch Engineering, 0.9×11 cm). The QS21/ PLGA was also pumped into the inlet of the static mixer at 7.5 mL/minute The outlet of the static mixer was connected to a prechilled stirred tank (hardening bath) with 12 L of prefiltered distilled water (MilliQ water, Millipore Corp.) at 2°–8° C. The pumping process was complete in 1 minutes 20 sec. The final microspheres were allowed to harden in the stirred tank for 1 hour at 2°–8° C. while nitrogen was passed across the liquid surface. After hardening, the microspheres were filtered through a 150- μm nylon mesh and then ultrafiltered in a 2.5-L Amicon stirred cell with a 20- μm stainless steel mesh (Tetko Corp.). The resulting microspheres were then diafiltered with 30 L of 0.1% Tween 20The microspheres were then dried by lyophilization or fluidized bed drying with nitrogen.

F. Microsphere Size Analysis

The apparent diameters of microspheres in water were measured by using a Brinkmann Particle Size Analyzer Model 2010 (Lens A, 1 to 150 μm range).

G. Scanning Electron Microscopy of Microspheres

The size and appearance of the dried microspheres were analyzed using Phillips Model 525M SEM. The microspheres were coated to a thickness of 10 nm with gold-palladium using HummerXP, Anatech.

H. Microsphere Loading and Release Characteristics for MN RGP120

The protein content of the MN rgp120-PLGA microspheres was determined as follows. Dried microspheres were added (10 to 20 mg) to 1 mL of 1N NaOH and allowed to dissolve by shaking at room temperature for 2 to 16 hours. Standards of rgp120 were prepared by adding 5N NaOH to the stock solution of MN rgp120 (1.5 mg/mL) to yield a 1N NaOH solution. In 1N NaOH, tyrosine is deprotonated resulting in a significant shift in the absorbance maximum and, thus, protein dissolved in 1N NaOH will have a different absorbance spectrum than native protein in buffer at neutral pH. Standard solutions containing different concentrations of MN rgp120 in 1N NaOH were used to determine the shifted absorbance maxima of the protein and the extinction coefficient at this wavelength. The extinction coefficient for MN rgp120 in 1N NaOH was 1.39 cm-1(mg/mL)-1 at 284 nm.

The amount of protein released from the microspheres was determined by the Pierce Chemical Co. BCA Protein Assay. Both dried and "wet" microspheres were analyzed. "Wet" microspheres were defined as microspheres that were removed from the diafiltration cell and suspended in release medium without additional processing. The amount of protein released was then used to calculate the percent of MN rgp120 released (percent of total) from the microspheres based on the mass of microspheres in the release device, the protein loading of the microspheres, and the volume of the release medium (20 mg of microspheres in 300 μl of 10 mM Hepes, 100 mM NaCl, 0.02% (w/w) Tween® 20, 0.02% NAN3, pH 7.4).

I. Determination Of QS2Microsphere Loading

The amount of QS21 encapsulated in the PLGA microspheres was determined by dissolving the microspheres in 1N NaOH at room temperature overnight. The completely dissolved solutions were neutralized with 6N HCl. The samples were then injected onto a SEC column, TSK G3000SW XL (0.78×30 cm), equilibrated in 0.4M KPO$_4$, pH 7.0 The column running conditions were the same as those used for the SEC analysis of rgp120. Since QS21 degrades in 1N NaOH, the chromatographs from SEC analysis contained several peaks. To quantify the total amount of QS21, the peak areas corresponding to QS21 and its degradation products were used in the determination of the core loading. As standards, known amounts of QS21 were added to placebo microspheres and then treated with 1N NaOH. SEC analysis was performed on the standards and the peak areas from the standards were used to calculate the amount of QS21 in each sample.

J. Determination of QS21 Release from Microspheres

QS21 released from microspheres was quantitated by a 5 μm YMC C4 (0.46×25 cm) RP-HPLC with 1 mL/minute flow rate and detection at 214 nm. A linear gradient was run in 15 minutes from 25 to 75% of solution B (Solution A: 0.1% TFA in water; Solution B: 0.1% TFA in 90% acetonitrile). QS21 controls were also run. In RP-HPLC analysis, the rgp120 peak elutes before the QS21 peak and, therefore, this method provides simultaneous quantitation of QS21 and rgp120 released from the microspheres.

K. Guinea Pig Studies

Guinea pigs (Hartley strain) were supplied by Charles River Laboratories. The animals were immunized by subcutaneous administration (200 μl) of the formulations. After immunization, the animals were bled by cardiac puncture at weeks 4, 6, 8, 14, and 20. The animal sera from each group (five animals per group in each experiment) at a given time point were pooled and analyzed for antibodies to MN rgp120 or the V3 loop of MN rgp120. The antibody assays were performed by ELISA methods by using either MN rgp120 or the linear peptide of the V3 loop of MN rgp120 as the coat protein on the microtiter plates. The antibody titers were determined by serial dilution of the samples. The endpoint titer value was defined as the dilution factor that resulted in a value two fold over the background and was determined by interpolation of the serial dilution values.

In separate studies, guinea pigs were immunized subcutaneously (200 μl) at 0, 1, and 2 months with different formulations. After 70 days, the animals were bled by cardiac puncture. The sera from each group were pooled and analyzed for ability to neutralize both the MN and ALA-1 strains of HIV-1. The virus strains were prepared from infected H9 cells. An inoculation titer of virus sufficient to completely kill cells in 7 days was incubated with serial dilutions (3 fold) of the test sera, and then added to MT4 T-lymphoid cells in 10% FCS/RPMI-1640 cell culture media. The cultures were incubated at 37° C. for 7 days and the cell viability was then quantitated by the MTT dye assay with optical density measurements at 570–650 nm (Mosmann, *J. Immunol. Methods* 65:55–63, [1983]). The endpoint titer values for the virus neutralization were defined as the dilution factor that resulted in an optical density reading two fold over the background of unprotected (killed) cells. These titers were typically twice those calculated at 50% protection.

L. Encapsulation of MDP

The encapsulation of MDP in PLGA was performed by the water-in-oil-in-water method. MDP (25 mg) was dissolved in 1 mL 4% carboxyl methyl cellulose (CMC) with phosphate buffered saline. PLGA (12 kDa, 0.2 IV, 65:35 lactide:glycolide, Lot# MPE 93-2) was supplied by MTI. Three grams of PLGA were dissolved in 6 mL of ethyl acetate. The MDP solution was then injected into the PLGA solution at 1° C. while homogenizing at 15,000 rpm. After injection of the MDP, the PLGA solution was homogenized for 1 minute. The homogenized MDP/PLGA solution was then emulsified with PVA to form the microspheres. This emulsification step was performed by pumping 9% PVA (10% ethyl acetate, 3° C.) at 1.5 L/minute into a static mixer (Koch Engineering, 0.9×11 cm, 6 mixing elements). The MDP/PLGA was also pumped into the inlet of the static mixer at 18 mL/minute. The outlet of the static mixer was connected to a prechilled stirred tank (hardening bath) with 12 L of prefiltered distilled water (MilliQ water, Millipore Corp.) at 2°–8° C. The pumping process was complete in 20 sec. The final microspheres were allowed to hardening in the stirred tank for 1 hour at 2°–8° C. while nitrogen was passed across the liquid surface. After hardening, the microspheres were filtered through a 150 μm nylon mesh and then ultrafiltered in a 2.5-L Amicon stirred cell with a 20 μm stainless steel mesh (Tetko Corp.). The resulting microspheres were then diafiltered with 30 L of 0.1% Tween 20 The microspheres were then analyzed for loading and release characteristics.

M. Production of Placebo Microspheres

Placebo microspheres were made as controls for the MDP and QS21 formulations. The placebo microspheres for the MDP formulation were made from 12 kDa PLGA (MTI, 50:50 lactide:glycolide, Lot# 622–84) with a method similar to the MDP encapsulation described above. The other placebo microspheres were prepared with the same PLGA formulations and under similar conditions to the QS21 microspheres.

N. Quantitation of MDP Release from Microspheres

The amount of MDP released from the microspheres was quantitated by using a 5 μm Vydac C18 column (0.46×15 cm). The column was operated at a flow rate of 0.7 mL/minute and peaks were detected by monitoring absorbance at 214 nm. Isocratic elution conditions of 2% methanol in 0.1M sodium phosphate, pH 3.0 resulted in two peaks, one at 5.6 minutes and another at 9.2 minutes. As the peak that eluted at 5.6 minutes did not resolve from the release media peak, the peak at 9.2 minutes was used as the measure of MDP released.

II. Results

Process Modifications for Improved Loading, Efficiency, and Initial Burst

These and other encapsulation studies revealed an empirical correlation between encapsulation efficiency (E), which is the ratio of experimental and theoretical protein loading, and the composition of the first phase:

$$E \propto \frac{\mu_p}{(V_a/V_o) TV_{MeCl_2}} \quad (1)$$

where $\mu_p$ is the viscosity of the polymer phase, $V_a/V_o$ is the volume ratio of aqueous to organic solutions in the first emulsion, $V_{MeCl_2}$ is the volume of methylene chloride in the second emulsion prior to polymer addition, and T is the temperature of the first and second emulsions. As indicated in previous studies, increasing the polymer concentration in the first phase from 0.1 to 0.3 g PLGA/mL methylene chloride yielded a two-fold increase in encapsulation efficiency (to about 40%).

To further increase the encapsulation efficiency and loading, the effect of temperature on gp120 encapsulation was studied. These studies were performed with a 50:50 mass ratio of 12 kDa and 100 kDa PLGA (75:25 lactide:glycolide, Boehringer Ingelheim) at a polymer concentration of 0.3 g/mL and an aqueous to organic volume ratio of 0.1 mL/mL. At these conditions, the encapsulation efficiency was 22% for room temperature operation and 55% for low temperature operation (0° C., Table 2). These results indicated that a reduction in operating temperature dramatically increased the process efficiency. The protein loading was also increased from 1.2 to 2.8% (w/w) by operation at the lower temperature. The reduced temperature of the first emulsion increases the viscosity of the polymer solution and reduces the propensity of the aqueous droplets to coalesce. The second emulsion can also be stabilized by the reduced temperature because the embryonic microspheres are less sensitive to shear forces. In both cases, the lower temperature should further stabilize the protein solution by freezing it into small droplets which are created during homogenization.

from the second emulsion causes more rapid extraction of the solvent from the microspheres and, thereby, allows the microspheres to harden more quickly, thereby entrapping a larger amount of protein.

To further confirm these observations, a different polymer system was used at the same conditions. This polymer blend, 50:50 mass ratio of 18 kDa and 100 kDa PLGA (75:25 lactide:glycolide, MTI), was less viscous in methylene chloride than the previous blend at the same concentration of 0.3 g/mL. Therefore, the encapsulation efficiency at room temperature with methylene chloride in the second emulsion was only 11%. By decreasing the operation temperature to 0° C. and removing the methylene chloride from the second emulsion, the encapsulation efficiency was increased to 86%. These changes also increased the protein loading from 0.6 to 4.4% (w/w) (Table 2). In addition, the initial burst from the wet (analyzed immediately after the production), lyophilized and vacuum dried microspheres was significantly decreased by reducing the operating temperature and removing the excess methylene chloride from the second emulsion (Table 2). The initial burst at low protein loading (less than 10% w/w) can be empirically correlated to the inverse of the encapsulation efficiency as defined in Equation 1. By decreasing the process temperature and removing excess solvent, the process efficiency, protein loading and initial burst were improved.

Equation 1 also indicates that the encapsulation efficiency is increased by increasing the viscosity of the polymer phase

TABLE 2

Effect of Temperature and Excess Methylene Chloride on the Encapsulation Efficiency, Loading, and Initial Burst[a]

| Process Conditions | Protein Loading (% w/w) | E(%) | Initial Burst (1 hr)[b] | | |
|---|---|---|---|---|---|
| | | | wet | lyo | vac |
| 12/100 kDa (75:25) BI[c] | | | | | |
| with MeCl$_2$[d], RT[e] | 1.2 | 22 | 21 | 75 | 68 |
| with MeCl$_2$, 0° C. | 2.8 | 55 | 23 | 42 | 53 |
| No MeCl$_2$, 0° C. | 4.9 | 96 | 10 | 32 | ND[f] |
| 18/100 kDa (50:50) MTI[c] | | | | | |
| with MeCl$_2$[d], RT[e] | 0.6 | 11 | 23 | 64 | 52 |
| No MeCl$_2$, 0° C. | 4.4 | 86 | 16 | 33 | ND[f] |

[a]Microspheres were prepared as described in the text.
[b]The microspheres were analyzed for release of gp120 either after production while still wet or after drying by lyophilization (lyo), or vacuum (vac, 5° C. for 1 week).
[c]A 50:50 mass ratio of the low and high molecular weight PLGA was used to produce these microspheres.
[d]The second emulsion (reaction kettle with 10% PVA) was either saturated with methylene chloride 1.5% or did not contain methylene chloride prior to the addition of the first emulsion.
[e]RT denotes room temperature (about 25° C.). Temperature corresponds to the operating temperature of both the first and second emulsions.
[f]ND denotes not determined.

The effect of methylene chloride saturation in the second emulsion was also investigated. As the amount of methylene chloride in the second emulsion prior to polymer addition is reduced, the encapsulation efficiency should increase (Equation 1). The same conditions that were used in the temperature study were applied to this analysis. The encapsulation was performed at 0° C. with the second emulsion either saturated with methylene chloride (1.5%) or without methylene chloride. Removal of excess methylene chloride from the second emulsion increased the encapsulation efficiency from 55% to 96% (protein loading: 2.8 to 4.9% (w/w), see Table 2). These results indicate that the second emulsion does not require methylene chloride prior to polymer addition. The removal of excess methylene chloride and decreasing the ratio of aqueous to organic volumes in the first phase. The viscosity of the first phase increases with increasing polymer concentration (g PLGA/mL methylene chloride) and molecular weight. To investigate the relationship between polymer molecular weight and the encapsulation efficiency, microspheres were produced by using several polymers with the same process conditions ($V_a/V_o$=0.1, 0.3 g/mL PLGA, reduced temperature, no excess methylene chloride). The initial studies were performed to evaluate differences in viscosity of the polymers from two separate vendors. A blend of an equal mass ratio of high and low molecular weight polymers from each supplier, MTI and BI, was used for microencapsulation. The microspheres made from 12 kDa and 100 kDa (75:25 lactide:glycolide) PLGA from BI yielded a protein loading of 5.0% (w/w) and an encapsulation efficiency of 98%. The microspheres produced with 18 kDa and 100 kDa (50:50 lactide:glycolide) PLGA from MTI yielded a slightly lower protein loading (4.4% w/w) and a reduced encapsulation efficiency (86%, Table 3). The initial burst from both preparations after lyophilization was equivalent (32 to 37%). These results indicated that there were not significant differences between the polymers from different vendors at these conditions.

$$L = \frac{1}{\left\{ \frac{[PLGA]}{V_d/V_o[gp120]} + 1 \right\}} = \frac{\text{Total } gp120}{(\text{Total } gp120 + PLGA)} \quad (2)$$

where L is the theoretical loading (gp120 mass fraction of total), [PLGA] is the PLGA concentration (g PLGA/mL methylene chloride) in the first phase, and [gp120] is the gp120 concentration (g/mL) in the aqueous solution injected into the first phase. Therefore, under these conditions, the

TABLE 3

Correlation Between Polymer Properties and Encapsulation Efficiency, Loading, and Initial Burst[a]

| Polymer | Protein Loading | | Initial Burst (1 hr)[b] | | |
|---|---|---|---|---|---|
| (lactide/glycolide) | (% w/w) | E(%) | wet | lyo | vac |
| 12 kDa (50:50) BI | 3.0 | 58 | 43 | 70 | 67 |
| 12 kDa (75:25) BI | 2.4 | 47 | 36 | 61 | 57 |
| 12/100 kDa (75:25) BI[c] | 4.9 | 96 | 10 | 32 | ND[d] |
| 12/100 kDa (75:25) BI[c] | 5.0 | 98 | 8 | 37 | 71 |
| 18 kDa (50:50) MTI | 2.4 | 92 | 6 | 49 | ND |
| 18 kDa (75:25) MTI | 2.5 | 96 | 6 | 36 | 24 |
| 100 kDa (75:25) MTI | 5.1 | 100 | 2 | ND | 18 |
| 18/100 kDa (50:50) MTI[c] | 4.4 | 86 | 16 | 33 | ND |

[a]Microspheres were prepared as described in the text.
[b]The microspheres were analyzed for release of gp120 either after production while still wet or after drying by lyophilization (lyo), or vacuum (vac, 5° C. for 1 week).
[c]A 50:50 mass ratio of the low and high molecular weight PLGA was used to produce these microspheres.
[d]ND denotes not determined.

In addition, the molecular weight and composition of the PLGA was investigated for its effect on encapsulation efficiency. Low molecular weight polymers from both vendors were analyzed. Microspheres produced from 12 kDa (75:25 lactide:glycolide) or 12 kDa (50:50 lactide:glycolide) PLGA from BI were only slightly different in their final characteristics. Both preparations of microspheres were produced under the same conditions ($V_d/V_o$=0.1, 0.3 g/mL PLGA, reduced temperature, no excess methylene chloride). By using the 12 kDa (75:25 lactide:glycolide) PLGA, an encapsulation efficiency of 47% was achieved and the microspheres had a protein loading of 2.4% w/w. These microspheres also had a moderate initial burst for the material which had not been dried (36% for wet microspheres, Table 3). By using the 12 kDa (50:50 lactide:glycolide) PLGA, an encapsulation efficiency of 58% was obtained and the protein loading was 3.0% w/w. Although the 12 kDa (50:50 lactide:glycolide) PLGA had a slightly better loading, the initial burst was greater (43%) and, therefore, the loading of the microspheres after the initial burst was nearly equivalent (1.5% w/w for 75:25 lactide:glycolide and 1.7% w/w for 50:50 lactide:glycolide). In both cases, the encapsulation efficiency was significantly lower than the equal mass ratio blend of high and low molecular weight PLGA (Table 3).

To increase encapsulation efficiency, the viscosity of the low molecular weight polymer solutions was increased by increasing the polymer concentration to 0.6 g/mL. Increasing the polymer concentration without increasing the amount of gp120 added to the first phase results in a reduction of the theoretical protein loading. This relationship is described by a simple mass balance on the components in the system:

increase in PLGA concentration from 0.3 to 0.6 g/mL decreased the theoretical loading by about one half to 2.6%. These experiments were performed with the low molecular weight polymers (18 kDa) obtained from MTI. For both the 50:50 and 75:25 lactide:glycolide 18 kDa PLGA, the encapsulation efficiency was dramatically improved (92 to 96%) and the protein loading was 2.4 to 2.5% w/w (Table 3). In addition, the initial bursts from both preparations were nearly equivalent and the lyophilized material had a moderate initial burst (Table 3). Therefore, a high encapsulation efficiency (greater than 90%) was achieved with the low molecular weight PLGA when the PLGA concentration in the first phase was increased to 0.6 g/mL. These results further validate Equation 1 since the increased viscosity of the first phase was achieved by increasing the PLGA concentration.

Unlike the low molecular weight PLGA, the high molecular weight PLGA (100 kDa) was very viscous in methylene chloride at 0.3 g/mL. Microencapsulation of μgp120 in 100 kDa (75:25 lactide:glycolide) PLGA from MTI at 0.3 g/mL ($V_d/V_o$=0.1, reduced temperature, no excess methylene chloride) resulted in 100% encapsulation of the protein and a protein loading of 5.1% w/w. These microspheres also had a very low initial burst even after drying (Table 3). Because the high molecular weight PLGA is much more viscous than the low molecular weight PLGA, a blend of both polymers should provide sufficient viscosity to allow encapsulation at 0.3 g PLGA/mL methylene chloride and decrease the large initial burst obtained when using the low molecular weight PLGA. To test this hypothesis, equal mass ratios of high and low molecular weight PLGA from both vendors were used to microencapsulate gp120 as described above. These preparations were produced with a high encapsulation efficiency (greater than 85%) and both lyophilized preparations had lower initial bursts than the microspheres made with only low molecular weight PLGA.

Increasing viscosity of the first emulsion through changes in the polymer (concentration or molecular weight) or reductions in temperature results in an increase in the size of the final microspheres. In general, the correlation between microsphere diameter, D, and process parameters is empirically described by:

$$D \propto \frac{\mu_p}{\omega_r T V_{MeCl_2}} \quad (3)$$

where $\omega_r$ is the stir speed in the second emulsion (rpm).

When the temperature was reduced to 0° C. and excess methylene chloride was added to the second emulsion, the microsphere diameter did not change for the preparations that were made with a blend of the low and high molecular weight polymers (Table 4). However, if the temperature of the emulsions was reduced and the excess methylene chloride was removed, the diameter of the microspheres produced with the same conditions was increased by a factor of two. Increasing the PLGA concentration from 0.3 to 0.6 g/mL also resulted in a doubling of the microsphere diameter, assuming that the low molecular weight PLGA from BI or MTI yields about the same diameter under the same process conditions (Table 4). The high molecular weight PLGA (100 kDa, MTI) was more viscous in the methylene chloride phase and the diameter of the microspheres produced with this polymer was three times greater than the low molecular weight PLGA, even though the impeller speed in the second emulsion was increased slightly. Reducing the impeller speed by 1000 rpm produced microspheres that were 50% larger for the low molecular weight PLGA (18 kDa, MTI). The equal mass ratio blends of low and high molecular weight PLGA were about twice the diameter of microspheres that were made from the low molecular weight PLGA with the same process conditions. Because increases in the viscosity of the first phase, reductions in temperature, and removal of excess methylene chloride are necessary to improve the encapsulation efficiency, the impeller speed in the second emulsion is preferably at its maximum (2500 rpm) to produce small microspheres (less than 20 μm).

B. Effect of Driving on Initial Burst and Quality of The Microspheres

To investigate the correlations among the initial burst, polymer, and drying technique, drying experiments were performed on several microsphere preparations. The drying techniques used in these studies were lyophilization, vacuum drying, and nitrogen drying. The amount of initial protein released (1 hour incubation) from microspheres dried with each of these techniques was compared to the initial burst from microspheres that were analyzed immediately after production (wet). The microspheres analyzed without drying always had an initial burst that was less than microspheres dried by either drying method. When hydrated, the microspheres will hydrolyze and release the encapsulated protein and, thus, excess moisture is preferably removed at the end of the microsphere process. Prior to complete drying, the microspheres are fully hydrated, resulting in hydrolysis of the PLGA with subsequent release of protein at or near the surface. The formation of microspheres in the second emulsion will affect the amount of protein at or near the surface. Larger microspheres produced in the second emulsion would have a smaller initial burst since the surface area to volume ratio is decreased. The first technique used to assess these possible effects on degradation of the microspheres during drying was vacuum drying. Unfortunately, when vacuum dried microspheres are fully hydrated for several days (dried at 5° C. for 7 days) the protein can be released during the drying process. Therefore, the drying time is preferably be minimized to reduce the initial burst.

One method used to reduce the microsphere drying time was lyophilization, which usually requires only one to two days. Lyophilization or vacuum drying of the low molecular weight PLGA formulations resulted in 1.5 to 8-fold increase in the initial burst (Tables 2 and 3). Aqueous protein droplets encapsulated at or near the surface of the microspheres probably cause the initial burst from these microspheres. If the viscosity of the first emulsion is increased, the aqueous droplets formed during homogenization are less likely to coalesce. Thus, small droplets at or near the surface will release less total protein for microspheres containing the

TABLE 4

Effect of Initial Phase Viscosity on Microsphere Size[a]

| Polymer (lactide/glycolide) | [PLGA][b] (g/mL) | T[c] (°C.) | $V_{MeCl2}$[d] (mL) | $\omega_r$[e] (rpm) | Median Diameter[f] (μm) |
|---|---|---|---|---|---|
| 12 kDa (50:50) BI | 0.3 | 0 | 0 | 2000 | 10 |
| 12 kDa (75:25) BI | 0.3 | 0 | 0 | 2000 | 12 |
| 12/100 kDa (75:25) BI[g] | 0.3 | 0 | 0 | 2200 | 22 |
| 12/100 kDa (75:25) BI[g] | 0.3 | 0 | 0 | 2500 | 22 |
| 12/100 kDa (75:25) BI[g] | 0.3 | 0 | 13.5 | 2000 | 9 |
| 12/100 kDa (75:25) BI[g] | 0.3 | RT | 13.5 | 2000 | 9 |
| 18 kDa (50:50) MTI | 0.6 | 0 | 0 | 1200 | 34 |
| 18 kDa (75:25) MTI | 0.6 | 0 | 0 | 2200 | 22 |
| 100 kDa (75:25) MTI | 0.3 | 0 | 0 | 2500 | 31 |
| 18/100 kDa (50:50) MTI[g] | 0.3 | 0 | 0 | 2000 | 21 |
| 18/100 kDa (50:50) MTI[g] | 0.3 | RT | 13.5 | 2000 | 6 |

[a]Microspheres were prepared as described in the text.
[b]Concentration of PLGA dissolved in methylene chloride in the first phase.
[c]Temperature of both emulsions during production (RT denotes room temperature, about 25° C.).
[d]Volume of methylene chloride in the second emulsion prior to addition of the first emulsion. 13.5 mL of methylene chloride in 900 mL 10% PVA results in saturation. Impeller speed in the second emulsion.
[f]Median diameter (volume basis) measured by photointeruption method (Materials and Methods).
[g]A 50:50 mass ratio of the low and high molecular weight PLGA was used to produce these microspheres.

same total aqueous volume. To increase the viscosity of the first emulsion, the PLGA concentration in the methylene chloride can be raised. By increasing the PLGA (12 kDa) concentration from 0.3 to 0.6 g/mL, the initial burst from lyophilized or vacuum dried microspheres was reduced from greater than 50% to 30 to 50%. Initial microspheres produced at 0.3 g/mL 12 kDa (50:50 lactide:glycolide) PLGA in the first emulsion were also cracked and broken after lyophilization. During lyophilization, the microspheres are frozen and the excess water is removed by sublimation. The formation of ice crystals within the microspheres can contribute to cracking or complete fracture of the microspheres. The stability of the aqueous droplets can be increased by increasing the viscosity of the first emulsion through reductions in temperature and by removing the excess methylene chloride from the second emulsion, causing a more rapid formation of microspheres. When the process conditions were modified to include both these changes, the micro- Because the initial burst is controlled by the diffusion of protein out of the microspheres, the rate of release (initial burst) will be dependent upon the concentration difference between the bulk solution and the hydrated, accessible protein (surface protein). The amount of protein at the surface will also be reduced since the protein concentration in the aqueous droplets is reduced. In general, the initial release of gp120 from the microspheres is dependent upon the polymer molecular weight, the process conditions, and the drying method. To reduce the initial burst and physical degradation (e.g. cracking), gp120 microspheres are preferably prepared with either a blend of high and low molecular weight PLGA or high molecular weight PLGA at low temperature without excess methylene chloride in the second emulsion. These microspheres can then be lyophilized or nitrogen dried to produce a free flowing powder.

TABLE 5

Effect of Drying Method on Initial Burst[a]

| Polymer (lactide:glycolide) | Protein Loading[b] (% w/w) | Initial Burst (1 hr)[c] | | |
|---|---|---|---|---|
| | | wet | lyophilized | nitrogen |
| 12/100 kDa (50:50) BI[d] | 3.1 | 16 | 19 | 12 |
| | 3.5 | 5 | 22 | 10 |
| | 1.8 | 15 | 15 | 10 |
| | 1.8 | 19 | 23 | 22 |
| | 0.5 | 2 | 0.4 | 1 |
| 18/100 kDa (50:50) MTI[d] | 3.8 | 12 | 23 | 8 |
| | 3.9 | 9 | 32 | 17 |
| | 1.8 | 5 | 15 | 7 |
| | 1.8 | 7 | 13 | 4 |
| 100 kDa (50:50) MTI | 1.8 | 10 | 10 | 2.4 |

[a]Microspheres were prepared as described in Materials and Methods (0.3 g PLGA/mL methylene chloride, 0.1 mL protein solution/mL methylene chloride. reduced temperature, no excess methylene chloride in second emulsion).
[b]All preparations had greater than 95% encapsulation efficiency.
[c]The microspheres were analyzed for release of gp120 either after production while still wet or after drying by lyophilization, or nitrogen dried as described in Materials and Methods.
[d]A 50:50 mass ratio of the low and high molecular weight PLGA was used to produce these microspheres.

spheres were not broken or cracked after lyophilization or vacuum drying. However, both the vacuum dried and lyophilized microspheres had a large initial burst (greater than 65%). The large initial burst is likely the result of the instability of the first emulsion encapsulated within the microspheres. More aqueous droplets can accumulate at the surface if the polymer is warmed above 2° to 8° C. and, thus, provide the large initial burst that was observed in the intact microspheres.

In contrast, lyophilization did not cause cracking or breakage of microspheres produced with either an equal mass ratio blend of high and low molecular weight PLGA or high molecular weight PLGA alone when produced at low temperature without excess methylene chloride in the second emulsion. These microsphere preparations also did not have a large initial burst (less than 30%, Table 5). In addition, microspheres produced with the high molecular weight PLGA had a much lower initial burst after lyophilization or vacuum drying (Tables 3 and 5). Both the equal mass ratio blend of high and low molecular weight polymer and the high molecular weight polymer preparations did not reveal a correlation between protein loading and initial burst for loadings ranging from 1.8 to 3.9% w/w. However, at very low protein loading (0.5% w/w), microspheres produced with the same conditions had a greatly reduced initial burst.

Correlation Between Second Burst and Polymer Properties

Figure 8:
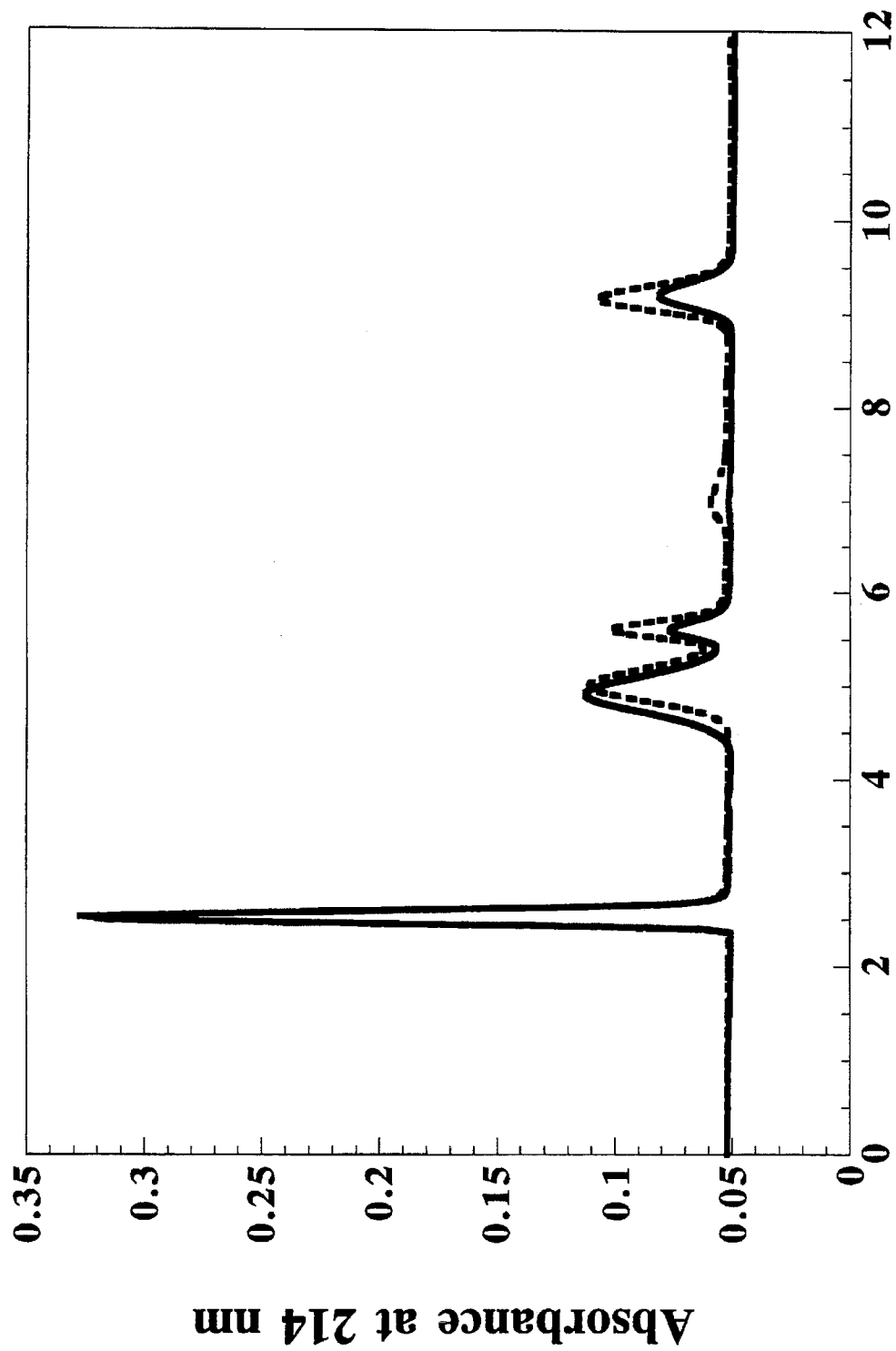
FIG. 8 is a reverse phase HPLC chromatogram comparing MDP released from PLGA microspheres to controls. The MDP eluted at (5.6 and 9.2 minutes); the additional peaks were from the release media (2.6 and 5.0 minutes) and the breakdown products of the PLGA (7.0 minutes). The solid line represents the control sample consisting of MDP incubated at 37° C. in release media with placebo microspheres. The dashed line represents the chromatogram for the MDP released initially from the PLGA microspheres.

Microspheres were produced by using PLGA of varying composition (lactide:glycolide) and molecular weight to assess the differences in the timing of the second burst. To obtain an in vivo autoboost of gp120 at the desired appropriate time (e.g., 1, 2, 3, or 4 months), the microspheres are preferably designed to produce an in vitro second burst at the same time (37° C., physiological buffer). The in vitro release characteristics of each preparation was studied until 80 to 100% of the total protein was released from the microspheres. All the preparations displayed a characteristic release profile: initial burst, minimal release (less than 10%), and second burst. A typical release profile for MN rgp120 PLGA microspheres is shown in FIG. 8. The release profile with the exception of the initial burst was not affected by the process conditions or drying, but the PLGA composition and molecular weight did have a significant impact. Bulk erosion of the microspheres is dependent upon the polymer composition (lactide:glycolide) and molecular weight and, therefore, the timing of the second burst resulting from bulk erosion is controlled by selecting the properties of the PLGA.

Figure 2:
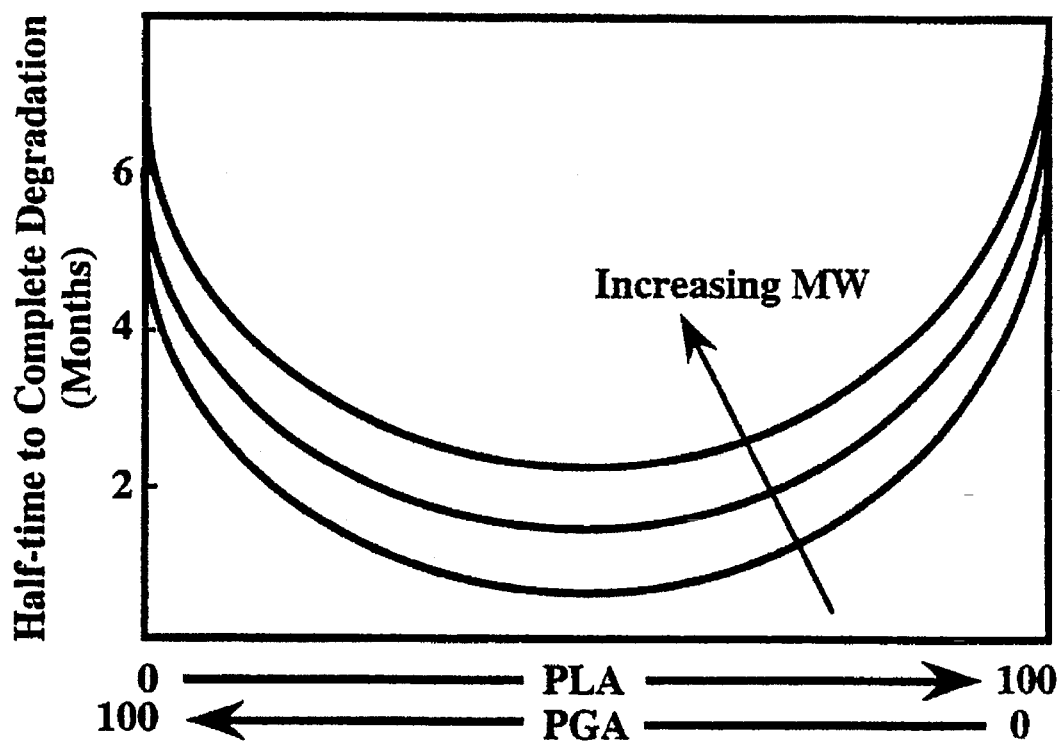
FIG. 2 is a diagram depicting in vivo degradation rate for PLGA polymers modified from Miller et al. (*J. Biomed. Mater. Res.* 11:711–719, 1977). The X-axis represents the relative ratio of either lactide or glycolide for each PLGA. The slowest degradation rates for a given polymer molecular weight occur for the polylactic acid (PLA) and polyglycolic acid (PGA) systems. The fastest degradation rate was achieved with PLGA containing an equal molar ratio of lactide and glycolide. The in vivo half-time to complete degradation was measured by histology studies in rats.

The in vitro release of MN rgp120 from PLGA microspheres correlates with the polymer properties as listed in Table 6. The microspheres produced from low molecular weight (12 or 18 kDa) PLGA with a 50:50 lactide:glycolide ratio had a second burst at 30 to 40 days, while microspheres made with the same molecular weight with a 75:25 lactide-:glycolide ratio did not undergo bulk erosion and release protein until 60 to 75 days. A similar dependence between lactide content and second burst timing was also obtained for microspheres made from high molecular weight (100 kDa) PLGA. The microspheres made from 100 kDa PLGA had a second burst at 60 to 70 and 90 to 100 days for the 50:50 and 75:25 lactide:glycolide ratios, respectively. The equal mass ratio blends of low and high molecular weight PLGA underwent bulk erosion with subsequent protein release at the same time as the corresponding low molecular weight polymer alone (Table 6). Therefore, the addition of high molecular weight PLGA to the low molecular weight PLGA at an equal mass ratio does not affect the timing of the second burst, but it does improve the encapsulation efficiency and decrease the initial burst as shown above. Microspheres produced with an equal mass ratio of low and high molecular weight PLGA should then be used if a one (50% lactide) or two (75% lactide) month autoboost is required. Alternatively, a two month autoboost can be obtained from microspheres made with the high molecular weight (100 kDa) PLGA with a 50:50 lactide:glycolide ratio. However, if a three month autoboost is needed, the microspheres could be produced with the high molecular weight (100 kDa) PLGA with a 75:25 lactide:glycolide ratio. These results confirm the previously observed relationship between in vivo degradation and polymer properties as depicted in FIG. 2. Thus, if a later autoboost (4 to 6 months) is desired, then polylactic acid (PLA), a high molecular weight PLGA with a high lactide (greater than 50%) content, or a higher molecular weight PLGA with 50% lactide (greater than 0.75 dL/g) is preferably used.

bination with 114 mg/mL MN rgp120 (20 mM Tris, 120 mM NaCl, pH 7.4) for the inner aqueous phase. By using these concentrated solutions, the aqueous-to-organic volume ratio was maintained constant (0.1 mL/mL) and moderate theoretical loadings were achieved (2 to 5% w/w). The QS21 phase was injected into the polymer phase and then the protein solution was added to avoid direct contact between the QS21/ethanol and MN rgp120 solutions prior to encapsulation. Microspheres prepared by this method with a 50:50 ratio of low (12 kDa) and high (100 kDa) molecular weight PLGA resulted in 100% encapsulation efficiency for the protein and only a 61.3% encapsulation efficiency for the QS21 (Table 7). Without limitation to any one theory, it is believed that the lower encapsulation efficiency for the QS21 could be the result of its surfactant properties. QS21 could accumulate at the aqueous/organic interface resulting in losses during the formation of the second emulsion and the final processing steps (hardening and washing). To reduce this possibility, 1% Tween® 20 was added to the QS21/ethanol formulation. Tween® is expected to also accumulate at the aqueous/organic interface and it is likely that Tween® will stabilize QS21 micelles. The QS21 encapsulation efficiency for microspheres produced by the same method with QS21/Tween®/ethanol was 80.6%. The addition of Tween® to the QS21 phase provided increased efficiency without adversely affecting the gp120 loading efficiency (100%). A completely efficient process for QS21 and gp120 coencapsulation was achieved with 20% Tween® in the QS21 phase and 12 kDa (75:25 lactide:glycolide) PLGA (Table 7).

To assess the encapsulation efficiency of QS21 alone, microspheres were prepared with the QS21/ethanol aqueous phase and 12 kDa (75:25 lactide:glycolide) PLGA. The volume ratio of aqueous to organic phase was reduced by

TABLE 6

Correlation between PLGA Properties and Second Burst[a]

| Polymer (lactide:glycolide) | Second Burst[b] Time (days) | % Released | Complete Erosion Time (days) |
|---|---|---|---|
| 12 kDa (50:50) BI[c] | 30–40 | 15 | 80 |
| 12 kDa (75:25) BI[c] | 60–75 | 15 | 90 |
| 18 kDa (50:50) MTI | 30–40 | 70 | 80 |
| 18 kDa (75:25) MTI | 40–70 | 80 | 80 |
| 100 kDa (50:50) MTI[d] | 60–70 | 50 | 100 |
| 100 kDa (75:25) MTI | 90–100 | 85 | 120 |
| 12/100 kDa (50:50) BI[e] | 30–40 | 80 | 80 |
| 12/100 kDa (75:25) BI[e] | 60–70 | 70 | 110 |
| 18/100 kDa (50:50) MTI[e] | 40–60 | 70 | 80 |

[a]Microspheres were prepared as described in Materials and Methods (0.3 g PLGA/mL methylene chloride, 0.1 mL protein solution/mL methylene chloride, reduced temperature, no excess methylene chloride in second emulsion).
[b]Second burst from microspheres was usually observed over one to two weeks. The time range listed is the initial and final days when the percent released was significant (greater than 10%/wk). The % released is the sum of all the protein released during the second burst.
[c]These microspheres had a large initial burst (greater than 50%) and, therefore, the amount of protein remaining at the second burst was reduced.
[d]The preparation of these microspheres was performed at room temperature and excess methylene chloride (1.5%) was used in the second emulsion. These process changes resulted in a large initial burst.
[e]A 50:50 mass ratio of the low and high molecular weight PLGA was used to produce these microspheres.

D. Development of Encapsulated QS21 Formulations

The coencapsulation of QS21 and MN rgp120 required changes in the process parameters. Because the aqueous-to-organic volume ratio affects the encapsulation efficiency and initial burst (Equation 1), the ratio could not be increased to compensate for the additional QS21 solution. A formulation of QS21 at 200 mg/mL in 50% ethanol was used in combination one half, which is equivalent to the volume of QS21 used in coencapsulation. The QS21 encapsulation efficiency at these conditions was 100% and, thus, a lower volume ratio produced the same increased efficiency as the addition of Tween®. Overall, QS21 can be coencapsulated with gp120 or encapsulated alone with a high efficiency (80 to 100%).

TABLE 7

Efficiency of Microencapsulation Processes for QS21-PLGA Microspheres[a]

| Formulation | % Loading (w/w)[b] | | Loading Efficiency (%) | |
|---|---|---|---|---|
| | QS21 | MN rgp120 | QS21 | MN rgp120 |
| 12/100 kDa (75:25)[c] | | | | |
| MN rgp120 + QS21 | 1.9 | 2.5 | 61.3 | 100 |
| MN rgp120 + QS21[d] 12 kDa (75:25) | 2.5 | 2.5 | 80.6 | 100 |
| MN rgp120 + QS21[e] | 3.1 | 2.5 | 100 | 100 |
| QS21[f] | 3.3 | — | 100 | — |

[a]Microspheres were prepared as described in Materials and Methods (0.3 g PLGA/mL methylene chloride, 0.1 mL aqueous solution/mL methylene chloride, reduced temperature, no excess methylene chloride in second emulsion, lyophilized).
[b]The mass fraction loading of QS21 and MN rgp 120 was determined by dissolution of the microspheres in 1 N NaOH. Subsequent analysis of the treated material is described in the Materials and Methods section.
[c]A 50:50 mass ratio of the low and high molecular weight PLGA was used to produce these microspheres.
[d]The QS21 phase in this formulation contained 1% Tween ® 20.
[e]This formulation consisted of QS21, 20% Tween ® 20, and 100 mM arginine in the QS21 aqueous phase injection (500 μl, see Materials and Methods).
[f]Microspheres produced at an aqueous to organic volume ratio of 0.05 mL/mL.

The microspheres were analyzed for the amount of the initial burst of QS21 and the effect of QS21 on the initial burst of MN rgp120As shown in Table 8, the initial burst from lyophilized microspheres was less than 30% for both the QS21 and the MN rgp120In addition, the coencapsulation of QS21 with rgp120 did not increase the initial burst of protein from the microspheres (see Tables 2 and 8). These studies indicate that microspheres with QS21 or QS21 and MN rgp120 can be prepared without a large initial burst of either antigen or adjuvant (less than 30%) and the integrity of the antigen is not compromised.

TABLE 8

Release of QS21 and MN rgp120 from PLGA Microspheres[a]

| Formulation | Initial Burst (%)[b] | | Second Burst[c] |
|---|---|---|---|
| | QS21 | MN rgp120 | Time (days) |
| 12/100 kDa (75:25)[d] | | | |
| MN rgp120 + QS21 | 19 | 29 | 60–75 |
| MN rgp120 + QS21[e] 12 kDa (75:25) | 24 | 21 | 60–75 |
| MN rgp120 + QS21[f] | 17 | 24 | 60–70 |
| QS21[g] | 18 | — | 60–70 |

[a]Microspheres were prepared as described in Materials and Methods (0.3 g PLGA/mL methylene chloride, 0.1 mL aqueous solution/mL methylene chloride, reduced temperature, no excess methylene chloride in second emulsion, lyophilized).
[b]The material released in the initial burst from the microspheres (1 hr., 37° C.) was analyzed by RP HPLC to determine the amount of QS21 and gp120.
[c]The second burst occurred over 7 to 14 days and the criteria for second burst for QS2) was greater than 2% intact QS21 released (see text for details).
[d]A 50:50 mass ratio of the low and high molecular weight PLGA was used to produce these microspheres.
[e]The QS21 phase in this formulation contained 1% Tween ® 20.
[f]This formulation consisted of QS21, 20% Tween ® 20, and 100 mM arginine in the QS21 aqueous phase injection (500 μl, see Materials and Methods).
[g]Microspheres produced at an aqueous to organic volume ratio of 0.05 mL/mL.

Another consideration for the QS21 microsphere formulations is the timing of the in vivo autoboost. Microspheres containing QS21, or QS21 with MN rgp120, were incubated in physiological buffer at 37° C. to assess the time for release of the second burst. As shown in Table 8, the second burst occurred over the same time range for both these microspheres and microspheres containing rgp120 alone (Table 6). In addition, the QS21 released from the microspheres after incubation in physiological buffer at 37° C. for 74 days was 25% intact. The amount of intact QS21 after the same time at the same conditions in solution would be less than 25% since the degradation rate of QS21 at pH 7.4 is twenty fold greater than pH 5.5 (40° C.) and the amount of intact QS21 remaining after 74 days at pH 5.5 and 40° C. is less than 50%. Thus, encapsulation of QS21 does not affect the timing of the second burst and can reduce the rate of QS21 degradation and clearance in vivo.

E. Immunogenicity of MN RGP120 Microspheres

Figure 5:
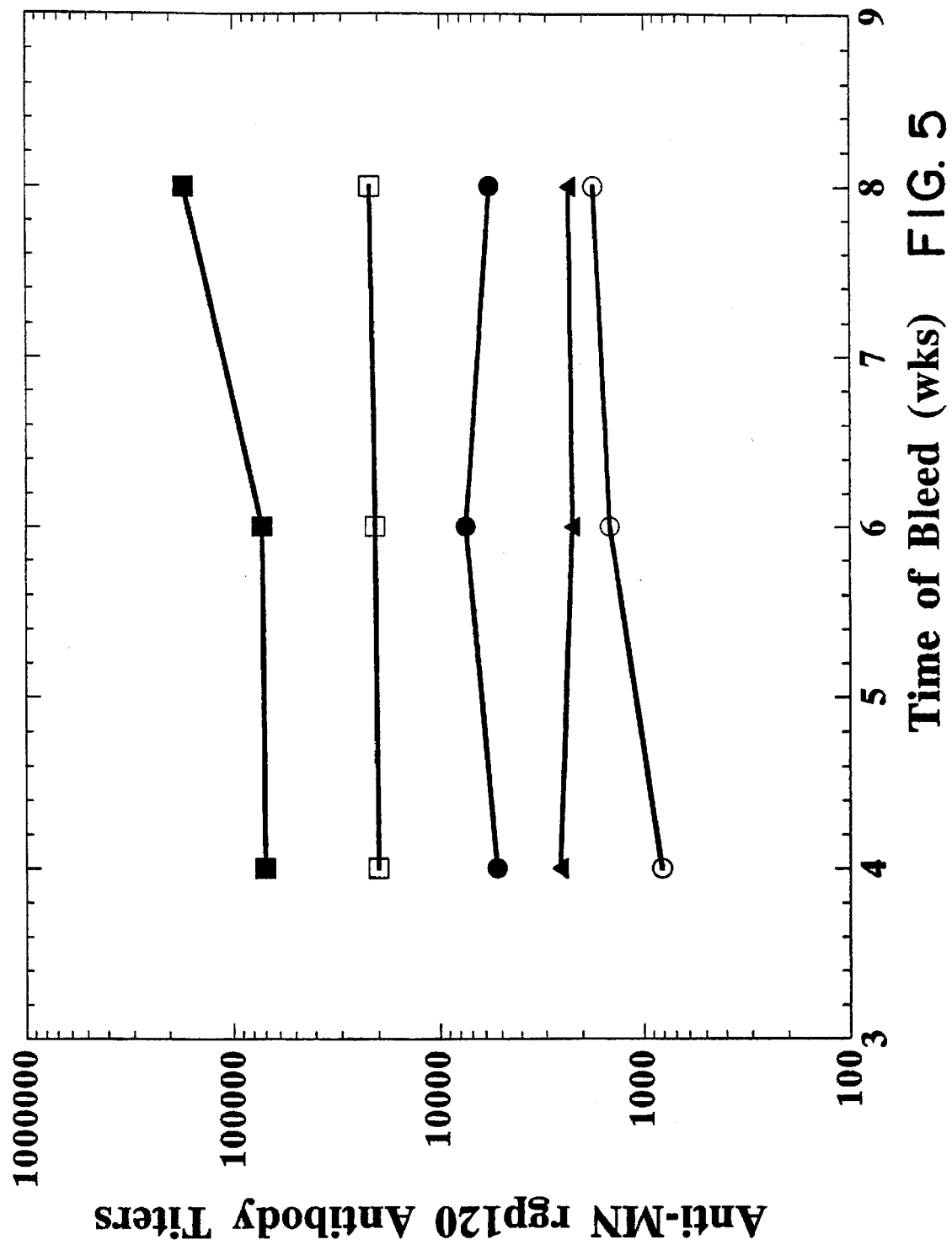
FIG. 5 is a graph depicting the effect of microencapsulation on the immunogenicity of MN rgp120 and QS21 as measured by antibody titers to MN rgp120. Guinea pigs were immunized at week 0 with MN rgp120 in different formulations: 15 µg of encapsulated and 15 µg of soluble MN rgp120 (○), 30 µg MN rgp120 with 60 µg alum (control, ▲), 30 µg of encapsulated MN rgp120 (●), 30 µg of encapsulated MN rgp120 and 50 µg of soluble QS21 (□), and 25 µg of encapsulated FIN rgp120 and 19 µg of encapsulated QS21 in the same microspheres (■). The MN rgp120 encapsulated formulation was produced with a 50:50 mass ratio blend of 12 kDa (75:25 lactide:glycolide) and 100 kDa (75:25 lactide:glycolide) PLGA from Boehringer Ingelheim (BI) (5.0 % w/w MN rgp120). The MN rgp120/QS21 encapsulated formulation consisted of both MN rgp120 and QS21 in the same microspheres which were made with a 50:50 mass ratio blend of 12 kDa (75:25 lactide:glycolide) and 100 kDa (75:25 lactide:glycolide) PLGA from BI (2.5% w/w MN rgp120, 1.9% w/w QS21).
Figure 6:
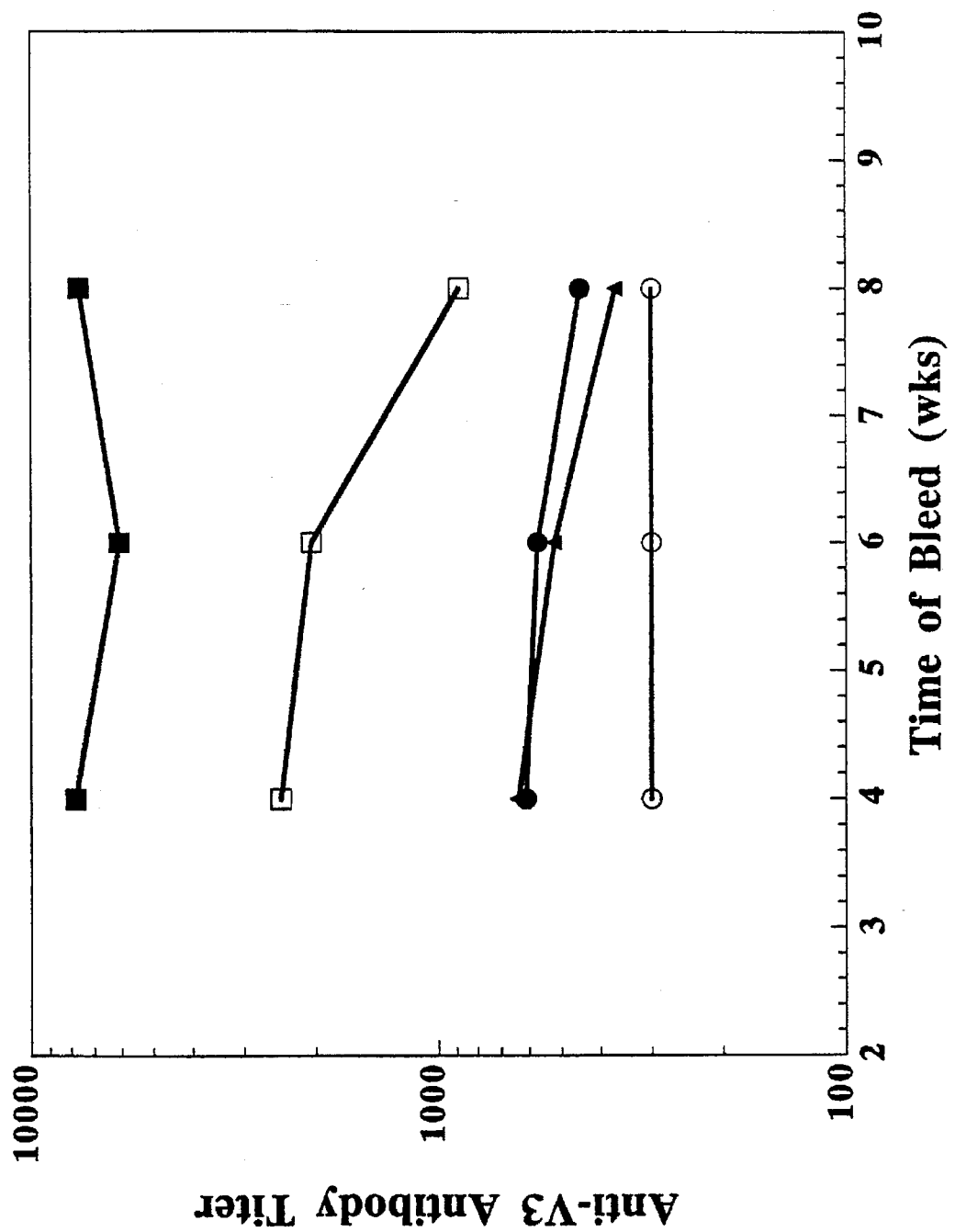
FIG. 6 is a graph depicting the effect of microencapsulation on the immunogenicity of MN rgp120 and QS21 as measured by antibody titers to the V3 loop of MN rgp120. Guinea pigs were immunized at week 0 with MN rgp120 in different formulations: 15 µg of encapsulated and 15 µg of soluble MN rgp120 (○), 30 µg MN rgp120 with 60 µg alum (control, ▲), 30 µg of encapsulated MN rgp120 (●), 30 µg of encapsulated MN rgp120 and 50 µg of soluble QS21 (□), and 25 µg of encapsulated MN rgp120 and 19 µg of encapsulated QS21 in the same microspheres (■). The MN rgp120 encapsulated formulation was produced with a 50:50 mass ratio blend of 12 kDa (75:25 lactide:glycolide) and 100 kDa (75:25 lactide:glycolide) PLGA from BI (5.0% w/w MN rgp120). The MN rgp120/QS21 encapsulated formulation consisted of both MN rgp120 and QS21 in the same microspheres which were made with a 50:50 mass ratio blend of 12 kDa (75:25 lactide:glycolide) and 100 kDa (75:25 lactide:glycolide) PLGA from BI (2.5% w/w MN rgp120, 1.9% w/w QS21).

To assess the ability of QS21 to increase the observed immune response to MN rgp120-PLGA, two different formulations were tested. One group of animals was immunized with 30 μg of MN rgp120 in a PLGA formulation (12/100 kDa (75:25 lactide:glycolide), 4.9% w/w protein, 32% initial burst) which was combined with 50 μg of soluble QS21Another group of animals was immunized with a formulation consisting of both MN rgp120 and QS21 encapsulated in the same microspheres. The microspheres with MN rgp120 and QS21 were produced with a 50:50 mass ratio of 12 kDa (75:25 lactide:glycolide) and 100 kDa (75:25 lactide:glycolide) PLGA. These microspheres had a protein loading of 2.5% (w/w) and a QS21 loading of 1.9% (w/w). The initial burst from these microspheres for protein and QS21 was 29% and 19%, respectively. The antibody titers of animals immunized with soluble QS21 and encapsulated MN rgp120 were four (anti-V3) to six (anti-MN rgp120) fold greater than titers of animals immunized with the encapsulated MN rgp120 alone (FIGS. 5 and 6). The amount of antigen released initially (9 μg) was the same for both of these groups since the same PLGA formulation was used. Therefore, soluble QS21 enhanced the immune response to encapsulated MN rgp120.

Since encapsulated MN rgp120 provided a greater immune response than soluble MN rgp120, additional enhancement in the immune response caused by the encapsulation of QS21 was examined. Animals were immunized with the PLGA formulation containing both MN rgp120 and QS21. The total antigen and QS21 dosed in the PLGA formulation were 25 μg and 19 μg, respectively. Both of these total doses were lower than the soluble and encapsulated controls because the protein and QS21 loadings were lower in these microspheres. As shown in FIGS. 5 and 6, the antibody titers of the group immunized with encapsulated MN rgp120/QS21 were an order of magnitude greater than the encapsulated MN rgp120 (30 μg dose) and alum control (30 μg dose) groups. In addition, the encapsulated MN rgp120/QS21 formulation only released 7.3 μg of MN rgp120 and 3.6 μg of QS21 in the initial burst. Therefore, a lower dose of both antigen and adjuvant in the encapsulated form was capable of yielding an order of magnitude greater immune response than the soluble or alum-formulated antigen.

To determine if the humoral response to MN rgp120 was sufficient to neutralize the virus upon infection, sera from guinea pigs immunized with MN rgp120 were analyzed for virus neutralization by using MT4 T-lymphoid cells which are very sensitive to HIV infection. The sera were taken from five different groups of guinea pigs, each immunized with a different formulation: 30 μg antigen with 60 μg alum, 30 μg antigen in Complete Freund's Adjuvant (CFA), 60 μg antigen with 50 μg QS21, 30 μg antigen with 50 μg QS21 and 60 μg alum, and 30 μg encapsulated antigen with 50 μg soluble QS21. The PLGA formulation was prepared from 12 kDa (50:50) PLGA. The microspheres had a protein loading of 1% (w/w) with an initial burst of 80% (lyophilized formulation). The animals were immunized with these formulations at 0, 1, and 2 months. Animals receiving CFA were boosted with incomplete Freund's adjuvant (IFA). The sera samples taken at day 70 were analyzed for virus neutralization.

As shown in Table 9, the MN virus neutralization titers from the group immunized with the MN rgp120-PLGA formulation and soluble QS21 were 50% greater than titers from the QS21/alum group and were 10 fold greater than the titers from the alum and CFA groups. The ALA-1 virus neutralization titer for the QS21/PLGA group was 60% lower than the QS21/alum group, but it was 8 fold higher than the alum group. The group immunized with the high antigen dose (60 µg) and soluble QS21 had the highest neutralization titers for both strains. However, the MN virus neutralization titer for the high-dose group was only slightly greater than the titers for the QS21/PLGA group. Therefore, MN rgp120 released from PLGA microspheres induced the formation of neutralizing antibodies to the MN and ALA-1 strains of HIV-1.

TABLE 9

Virus neutralization titers for sera from guinea pigs at day 70 after immunization with different formulations of MN rgp120 (30 µg MN rgp120/dose, immunizations at 0, 1, and 2 months).

| Formulation | Virus Neutralization Titer of RIV-1 strains | |
|---|---|---|
| | MN strain | ALA-1 strain |
| Alum (60 µg) | 325 | 2000 |
| CFA[a] | 200 | 25 |
| QS21 (50 µg)[b] | 3500 | 35000 |
| QS21 (50 µg) + Alum (60 µg) | 2200 | 25000 |
| QS21 (50 µg) + PLGA[c] | 3000 | 15000 |

[a]Complete Freund's adjuvant was prepared by emulsification with a syringe-to-syringe technique immediately prior to immunization.
[b]This group was immunized with 60 µg of MN rgp120 along with the soluble QS21.
[c]The encapsulated MN rgp120 (12 kDa (50:50) PLGA, 1% w/w MN rgp120) was mixed with soluble QS21 prior to immunization.

F. Continuous Release of MDP from Microspheres

Figure 7:
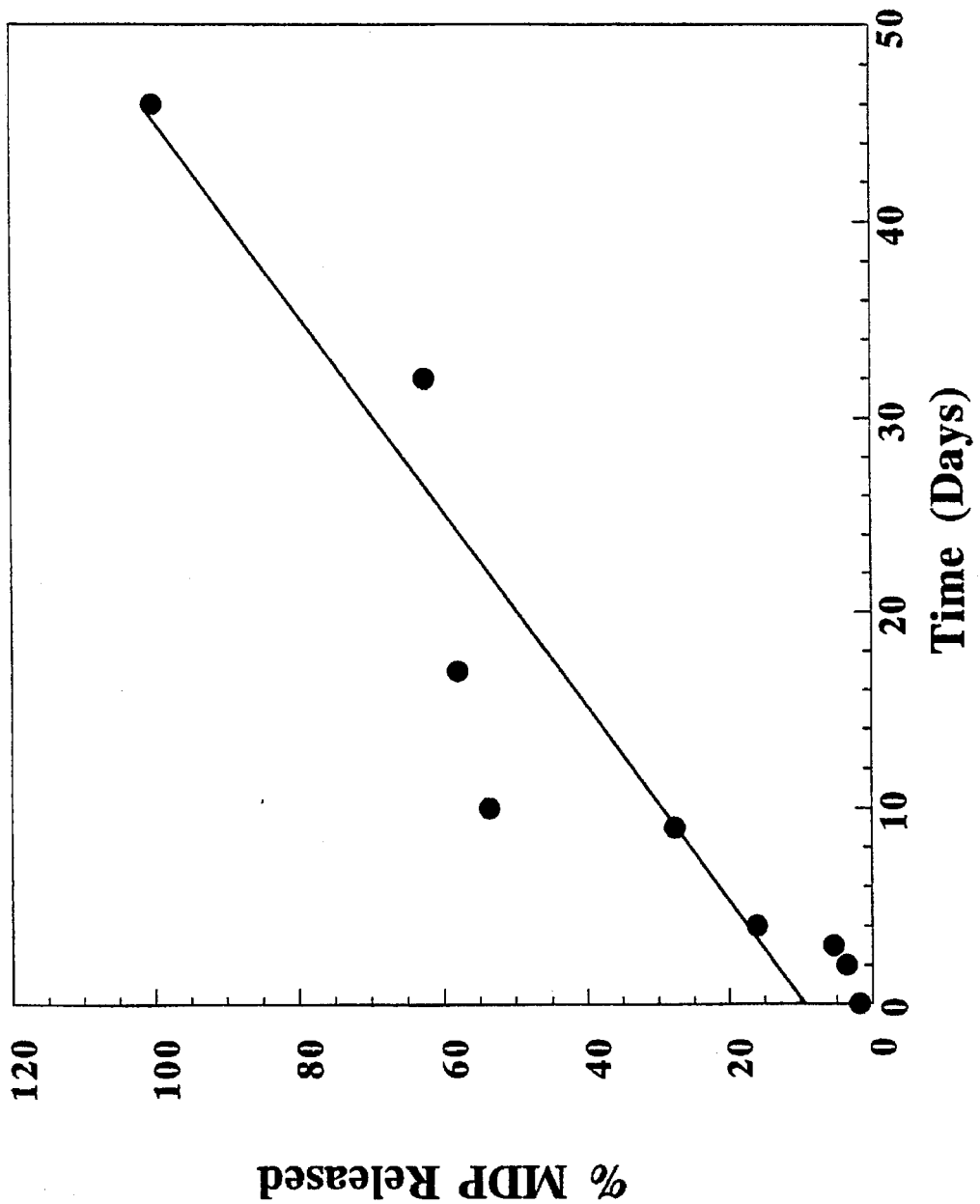
FIG. 7 is a graph depicting continuous release of muramyl dipeptide (MDP) from PLGA microspheres. PLGA (12 kDa, 65:35 lactide:glycolide, Medisorb Technologies International, L. P. (MTI) Lot# MPE 93-2) was used to produce microspheres with 0.8% (w/w) MDP. The microspheres were analyzed for loading and release immediately after production. The straight line has a slope of 2.03%/day with an R2 fit to the data of 0.934.

The encapsulation of MDP in PLGA microspheres resulted in an encapsulation efficiency of 96% with a core loading of 0.8% (w/w). As shown in FIG. 7, these microspheres had a small initial burst (less than 5% in 1 hr) and provided a 2% release of MDP per day over 46 days. To assess the effects of the encapsulation process on MDP, the initial release (1 hour) of MDP from the microspheres was assayed by reverse phase HPLC. Controls were also performed by incubating MDP in the release media at 37° C. with placebo microspheres (FIG. 8). MDP eluted as two peaks (5.64 minutes and 9.20 minutes). Additional peaks in the chromatogram were contributed by the release media (2.55 minutes and 5.04 minutes) and the breakdown products of PLGA (7.02 minutes). The MDP released from the microspheres was not altered by the encapsulation process.

G. Pulsatile Release Of QS21

Figure 9:
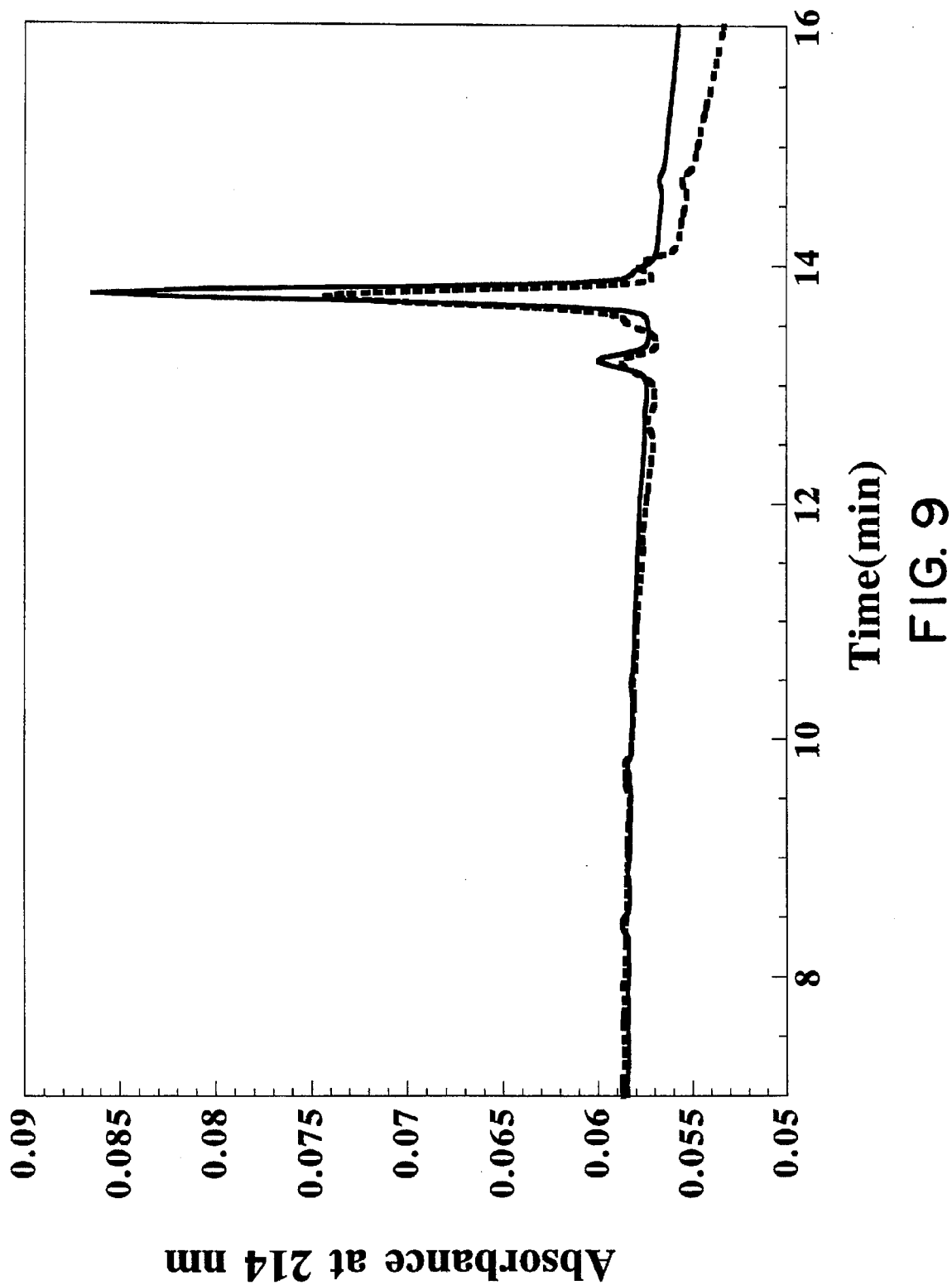
FIG. 9 is a reverse phase HPLC chromatogram comparing QS21 released from PLGA microspheres made with methylene chloride and a reaction kettle to controls. The species which eluted at 13. 4 and 13. 9 minutes are isomers of the intact QS21. Earlier eluting species are hydrolysis products from QS21. The solid line represents the control sample consisting of QS21 incubated at 37° C. in release media with placebo microspheres. The dashed line represents the chromatogram for the QS21 released initially from the PLGA microspheres.

The pulsatile release of QS21 was achieved by using a mixture of high and low molecular weight PLGA. The first formulation produced with methylene chloride and a reaction kettle consisted of a 50:50 mass ratio of 12 kDa (75:25 lactide:glycolide) and 100 kDa (75:25 lactide:glycolide) PLGA from BI. This formulation resulted in microspheres with 2.6% w/w loading and a low initial burst (7% w/w). The encapsulation efficiency from this process was only 46%. These microspheres had a second burst of QS21 at 60 to 75 days. The initial QS21 released was analyzed by reverse phase HPLC and controls were performed by incubating QS21 at 37° C. in release media with placebo microspheres. As shown in FIG. 9, the QS21 initially released from the microspheres was not degraded.

The second process for encapsulation of QS21 included the use of ethyl acetate instead of methylene chloride and a static mixer in place of the reaction kettle (1-liter fermenter). These microspheres were made with a 50:50 mass ratio of 12 kDa (65:35 lactide:glycolide) and 100 kDa (65:35 lactide:glycolide) PLGA from MTI. The QS21 loading was 1.9% w/w and the encapsulation efficiency was 29%. The reduced encapsulation efficiency was probably due to the larger volume of QS21 injected into the polymer phase (1.0 mL). The initial burst from these microspheres was small (less than 10%) and the second burst occurred between 50–65 days. The quality of the QS21 released from these microspheres was also analyzed by reverse phase HPLC (FIG. 10). The initial QS21 released was compared to controls with QS21 incubated at 37° C. in release media with placebo microspheres. The QS21 initially released from these microspheres contained a small amount of QS21hydrolysis products (less than 10%). Overall, the microencapsulation process did not significantly affect the quality of the QS21.

We claim:

1. A composition comprising polylactide or poly (D-L-lactide-co-glycolide) (PLGA) microspheres encapsulating an adjuvant capable of stimulating an immune response to an antigen of interest, wherein the volume of aqueous adjuvant incorporated into the polymer is equal to or less than 1 milliliter per 3 grams polymer;

the ratio of lactide to glycolide is from about 100:0 to 0:100 weight percent;

the inherent viscosity of PLGA polymers used in the microspheres is about 0.1 to 1.2 dL/g;

the median diameter of the microspheres is from about 20 to 100 µm; and the adjuvant is released from the microspheres in a triphasic pattern characterized by a first phase, wherein less than 30% of the adjuvant is released in an initial burst over a period of about one day, a second phase, following said first phase, wherein less than 10% of the adjuvant is released from the microspheres over a period of about 1 day and between about 30 and 200 days, and a third phase, following said second phase, wherein the remaining adjuvant is released in a second burst.

2. The composition of claim 1 wherein the median diameter of the microspheres is about 30 µm.

3. The composition of claim 1 wherein the adjuvant is a saponin.

4. The composition of claim 1 wherein the adjuvant is muramyl dipeptide.

5. The composition according to claim 1 wherein the second phase is over a period of about 30 days.

6. The composition according to claim 1 wherein the second phase is over a period of about 60 days.

7. The composition according to claim 1 wherein the second phase is over a period of about 90 days.

8. The composition according to claim 1 wherein the second phase is over a period of about 120 days.

9. The composition according to claim 1 wherein the second phase is over a period of about 180 days.

* * * * *